United States Patent [19]

Telfer

[11] Patent Number: 5,286,612
[45] Date of Patent: Feb. 15, 1994

[54] PROCESS FOR GENERATION OF FREE SUPERACID AND FOR IMAGING, AND IMAGING MEDIUM FOR USE THEREIN

[75] Inventor: Stephen J. Telfer, Arlington, Mass.

[73] Assignee: Polaroid Corporation, Cambridge, Mass.

[21] Appl. No.: 965,161

[22] Filed: Oct. 23, 1992

[51] Int. Cl.$^5$ .............. G03C 1/725; G03C 1/73; G03C 1/735; G03C 5/00
[52] U.S. Cl. .................... 430/335; 430/333; 430/336; 430/203; 430/269; 430/270
[58] Field of Search ............ 430/333, 336, 340, 346, 430/203, 269, 270; 204/157.45; 549/331, 332

[56] References Cited

U.S. PATENT DOCUMENTS

| | | | |
|---|---|---|---|
| 3,617,270 | 11/1971 | Kampfer | 430/62 |
| 3,915,706 | 10/1975 | Limburg et al. | 96/27 R |
| 3,932,514 | 1/1976 | Thelen et al. | 260/586 P |
| 4,092,146 | 5/1978 | Fischer et al. | 71/70 |
| 4,159,387 | 6/1979 | Bellus | 560/185 |
| 4,345,017 | 8/1982 | Cournoyer et al. | 430/221 |
| 4,508,811 | 4/1985 | Gravesteijn et al. | 430/270 |
| 4,602,263 | 7/1986 | Borrer et al. | 346/201 |
| 4,720,449 | 1/1988 | Borrer et al. | 430/338 |
| 4,826,976 | 5/1989 | Borrer et al. | 544/58.4 |
| 4,857,437 | 8/1989 | Banks et al. | 430/270 |
| 4,916,046 | 4/1990 | Doessel | 430/281 |
| 4,992,571 | 2/1991 | Fukuyama et al. | 566/64 |
| 5,037,575 | 8/1991 | Miura et al. | 430/70 |
| 5,055,376 | 10/1991 | Saeva | 430/270 |
| 5,084,371 | 1/1992 | Schwalm et al. | 430/270 |
| 5,102,771 | 4/1992 | Vogel et al. | 430/270 |
| 5,141,969 | 8/1992 | Saeva et al. | 430/270 |

FOREIGN PATENT DOCUMENTS 824630 10/1969 Canada .

OTHER PUBLICATIONS

Berry et al., Chemically Amplified Resists for I-line and G-line Applications, SPIE 1262, 575 (1990).
Bou et al., Tetrahedron Letters, 23(3), 361 (1982).
Cohen S. and Cohen, S. G., J. Am. Chem. Soc., 88, 5433 (1966).
Crivello et al., J. Polym. Sci., Polym. Chem. Ed., 16, 2441 (1978).
Dehmlow et al., Chem. Ber. 113(1), 1-8 (1979).
Dehmlow et al., Chem. Ber. 121(3), 569-71 (1988).
Islam, N. et al., Tetrahedron 43, 959-970 (1987).
Pericas et al., Tetrahedron Letters, (1977) 4437-38.
Reichmanis et al., Chemical Amplification Mechanism for Microlithography, Chem. Mater., 3(3), 394 (1991).

Primary Examiner—Charles L. Bowers, Jr.
Assistant Examiner—Geraldine Letscher
Attorney, Agent, or Firm—David J. Cole

[57] ABSTRACT

Acid can be generated by exposing a mixture of a superacid precursor and a dye to actinic radiation of a first wavelength which does not, in the absence of the dye, cause decomposition of the superacid precursor to form the corresponding superacid, thereby causing absorption of the actinic radiation and decomposition of part of the superacid precursor, with formation of a protonated product derived from the dye, then irradiating the mixture with actinic radiation of a second wavelength, thereby causing decomposition of part of the remaining superacid precursor, with formation of free superacid. Preferably, following these irradiations, the imaging medium is heated while the superacid is admixed with a secondary acid generator capable of being thermally decomposed to form a second acid, the thermal decomposition of the secondary acid generator being catalyzed by the presence of the superacid. The acid generation process may be used for imaging by bringing the superacid or second acid into contact with an acid-sensitive material which changes color on contact with acid, or the superacid may be used to trigger polymerization, depolymerization or other reactions.

18 Claims, 4 Drawing Sheets

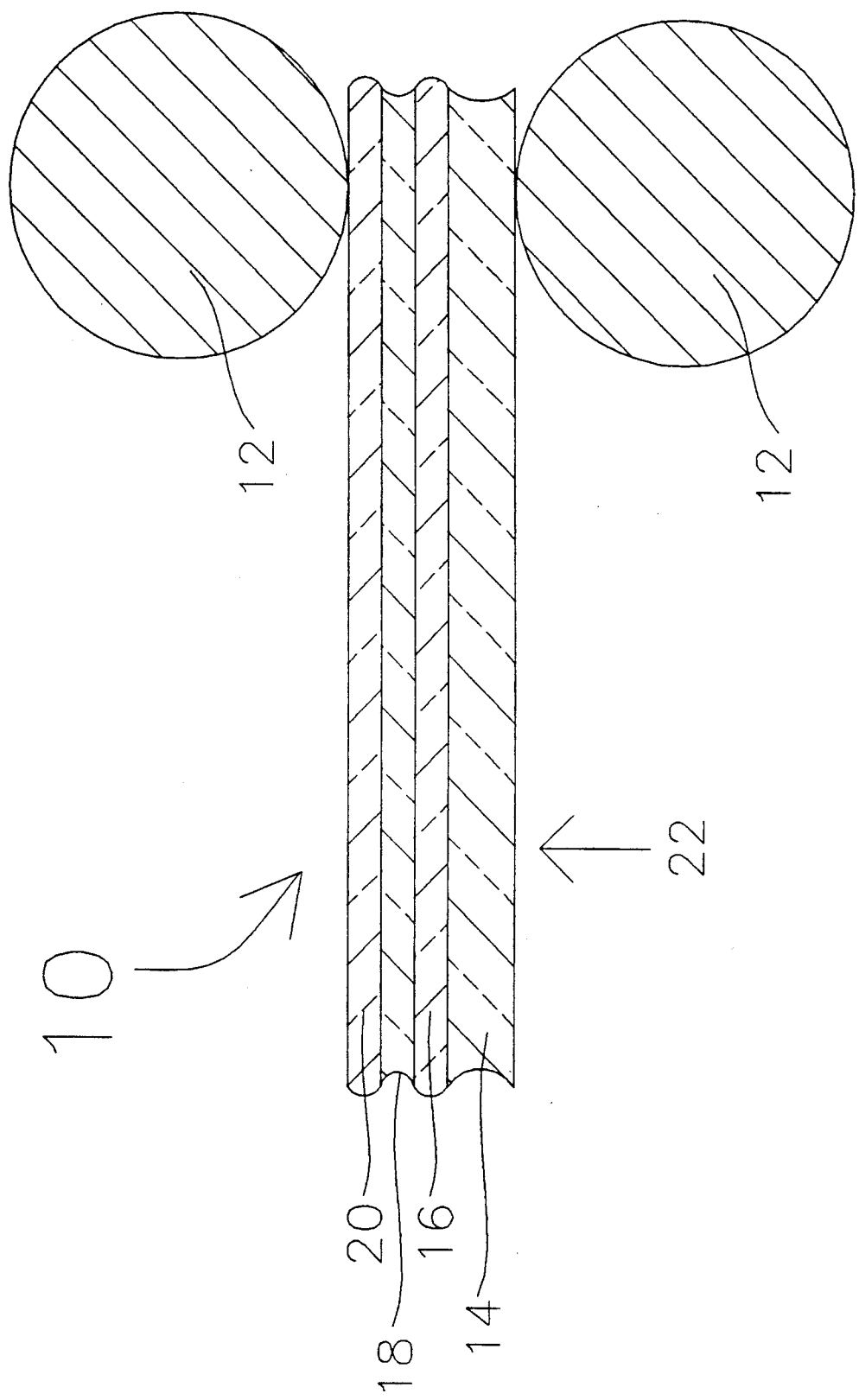

5,286,612

PROCESS FOR GENERATION OF FREE SUPERACID AND FOR IMAGING, AND IMAGING MEDIUM FOR USE THEREIN

REFERENCE TO RELATED APPLICATIONS

Attention is directed to copending Application Ser. No. 07/965,172 of even date herewith and assigned to the same assignee as the present application; this copending application describes and claims a process and imaging medium generally similar to those of the present invention, but in which the breakdown of a squaric acid derivative is initiated thermally.

Attention is also directed to copending Application Ser. No. 07/965,162 of even data herewith and assigned to the same assignee as the present application; this copending application describes and claims a process and imaging medium generally similar to those of the present invention but in which a superacid precursor is exposed to actinic radiation effective to generate superacid from the superacid precursor, and the resultant superacid is heated while admixed with a squaric acid derivative capable of thermally decomposing to produce an acid, thereby causing production of squaric acid or an acidic derivative thereof.

BACKGROUND OF THE INVENTION

This invention relates to a process for generation of acid and for imaging, and to an imaging medium for use in this imaging process.

Some conventional non-silver halide photosensitive compositions, for example photoresists, contain molecules which are inherently photosensitive, so that absorption of a single quantum brings about decomposition of only the single molecule which absorbs the quantum. However, a dramatic increase in the sensitivity of such photosensitive compositions can be achieved if the photosensitive molecule initiates a secondary reaction which is not radiation-dependent and which effects conversion of a plurality of molecules for each quantum absorbed. For example, photoresist systems are known in which the primary photochemical reaction produces an acid, and this acid is employed to eliminate acid-labile groups in a secondary, radiation-independent reaction. See, for example, U.S. Pat. Nos. 3,932,514 and 3,915,706; Reichmanis et al., Chemical Amplification Mechanism for Microlithography, Chem. Mater., 3(3), 394 (1991) and Berry et al., Chemically Amplified Resists for I-line and G-line Applications, SPIE, 1262, 575 (1990). Also, U.S. Pat. No. 5,084,371 describes a radiation-sensitive mixture which contains a water-insoluble binder which comprises a mixture of phenolic and novolak polymers and which is soluble or dispersible in aqueous alkali, and an organic compound whose solubility in alkaline developer is increased by acid, and which also contains at least one acid-cleavable group, and in addition a further group which produces a strong acid upon exposure to radiation.

U.S. Pat. No. 4,916,046 describes a positive radiation-sensitive mixture using a monomeric silylenol ether, and a recording medium produced therefrom. This patent also contains an extensive discussion of radiation-sensitive compositions which form or eliminate an acid on irradiation. According to this patent, such radiation-sensitive compositions include diazonium, phosphonium, sulfonium and iodonium salts, generally employed in the form of their organic solvent-soluble salts, usually as deposition products with complex acids such as tetrafluoroboric acid, hexafluorophosphoric acid, hexafluoroantimonic acid and hexafluoroarsenic acid; halogen compounds, in particular triazine derivatives; oxazoles, oxadiazoles, thiazoles or 2-pyrones which contain trichloromethyl or tribromomethyl groups; aromatic compounds which contain ring-bound halogen, preferably bromine; a combination of a thiazole with 2-benzoylmethylenenaphthol; a mixture of a trihalomethyl compound with N-phenylacridone; α-halocarboxamides; and tribromomethyl phenyl sulfones.

The aforementioned phosphonium, sulfonium and iodonium salts are superacid precursors which, upon exposure to ultraviolet radiation, decompose to produce superacids, that is to say acids with a $pK_a$ less than about 0. Other materials decompose to produce superacids in a similar manner. However, all the superacid precursors require ultraviolet to blue visible radiation for decomposition (see, for example, Crivello and Lam, Dye-Sensitized Photoinitiated Cationic Polymerization, J. Polymer Sci., 16, 2441 (1978)), and the need for this radiation is disadvantageous when it is desired to produce high resolution images, which are most conveniently produced by laser imaging. In the present state of technology, solid state diode lasers emitting at near infra-red wavelengths of about 700 to 1200 nm. provide the highest output per unit cost. YAG lasers emitting at about 1000–1200 nm. are also useful in imaging processes, while ultraviolet lasers are costly. Accordingly, it is desirable to find some way in which superacid precursors could be rendered susceptible to infra-red radiation in order that imaging of a superacid precursor-containing medium could be effected using an infra-red laser.

It is already known that various sensitizing dyes can catalyze the decomposition of superacid precursors upon exposure to wavelengths to which the superacid precursors are not sensitive in the absence of the sensitizing dye. Unfortunately, due to the difficulty of protonating the superacid anion consequent upon the very low $pK_a$ of the superacid, the sensitizing dye is protonated by the superacid, so that no free superacid is produced in the medium (i.e., the sensitizing dye buffers the superacid produced). Since no free superacid is released into the medium, these processes cannot be used to trigger any secondary reaction which requires the presence of unbuffered strong acid, such as the reactions used in many photoresists, as described in the aforementioned patents.

This invention provides a process for generation of acid which enables a medium containing a superacid precursor and a sensitizing dye, which is more easily protonated than the superacid anion, to be imaged with radiation of a frequency to which the superacid precursor is not sensitive, so as to produce free superacid in the medium. By including an acid-sensitive material in the medium, the process can be used for imaging.

SUMMARY OF THE INVENTION

Accordingly, this invention provides a process for generation of acid, which process comprises:

providing a medium containing a mixture of a superacid precursor and a dye capable of absorbing actinic radiation of a first wavelength which does not, in the absence of the dye, cause decomposition of the superacid precursor to form the corresponding superacid, the superacid precursor being capable of being decomposed by actinic radiation of a second wavelength shorter than the first wavelength;

irradiating the medium with actinic radiation of the first wavelength, thereby causing absorption of the actinic radiation, and decomposition of part of the superacid precursor, without formation of free superacid but with formation of a protonated product derived from the dye; and thereafter irradiating the medium with actinic radiation of the second wavelength, thereby causing decomposition of part of the remaining superacid precursor, with formation of free superacid.

In a preferred form of this process, only part of the medium is irradiated with the actinic radiation of the first wavelength, but a larger portion of the medium is irradiated with the actinic radiation of the second wavelength, such that free superacid is generated in the part of the medium exposed to the radiation of both the first and second wavelengths, but no free superacid is generated in the part of the medium exposed to the radiation of the second wavelength but not to the radiation of the first wavelength. Desirably, the medium is imagewise exposed to the actinic radiation of the first wavelength so that the free superacid generated forms an image.

This invention also provides an imaging medium comprising:

a superacid precursor; and a dye capable of absorbing actinic radiation of a first wavelength, the superacid precursor being decomposed to form a superacid by actinic radiation of a second wavelength shorter than the first wavelength, but not being decomposed by actinic radiation of the first wavelength in the absence of the dye, the superacid produced by decomposition of the superacid precursor being capable of forming a protonated product derived from the dye; and a secondary acid generator capable of being thermally decomposed to form a second acid, the thermal decomposition of the secondary acid generator being catalyzed in the presence of the superacid.

Finally, this invention provides an imaging medium comprising:

a superacid precursor and an infra-red dye capable of absorbing infrared radiation having a wavelength within the range of about 700 to about 1200 nm, the superacid precursor being capable of being decomposed by ultraviolet radiation having a wavelength in the range of about 180 to about 400 nm to form a superacid, the superacid precursor not being decomposed by infrared radiation having a wavelength within the range of about 700 to about 1200 nm in the absence of the infrared dye.

BRIEF DESCRIPTION OF THE DRAWINGS

FIG. 3 is a schematic cross-section through an imaging medium of the present invention as it is being passed between a pair of hot rollers during the imaging process of the present invention.

DETAILED DESCRIPTION OF THE INVENTION

Figure 1A:
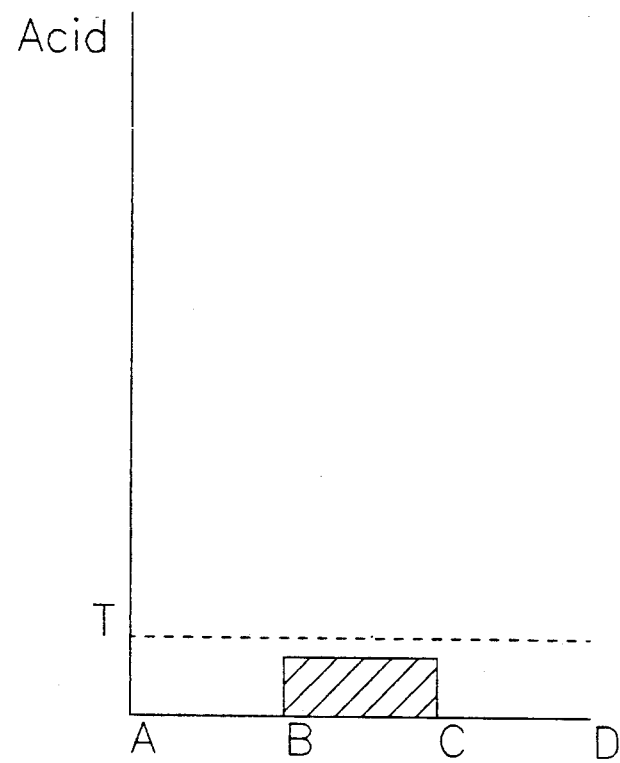
FIGS. 1A—1D show the acid concentrations in the exposed and unexposed regions of the imaging medium during the various steps of a preferred process of the present invention.

As already mentioned, the present process employs a medium containing a mixture of a superacid precursor and a dye. The dye (which may hereinafter be referred to as the "sensitizing dye") is capable of absorbing actinic radiation of a first wavelength which does not, in the absence of the sensitizing dye, cause decomposition of the superacid precursor to form the corresponding superacid; typically this first wavelength is in the range of about 700 to about 1200 nm, so that the sensitizing dye is a near infra-red dye. Also, the superacid precursor is capable of being decomposed by actinic radiation of a second wavelength shorter than the first wavelength; typically this second wavelength is in the range of about 400 to about 180 nm, so that the actinic radiation of the second wavelength can be conveniently supplied by ultraviolet sources (e.g., a mercury arc lamp) which are readily available and will be familiar to those skilled in the art.

As is well known to those familiar with superacid precursors, superacid precursors may require the presence of a precursor sensitizer, typically a polycyclic hydrocarbon such as pyrene, to enable the superacid precursor to break down upon irradiation with ultraviolet or other actinic radiation, thereby producing superacid. Accordingly, references herein to a superacid precursor shall be construed to refer to a mixture of superacid precursor and precursor sensitizer, if the superacid precursor is one which requires the presence of such a precursor sensitizer.

The medium is first irradiated with actinic radiation of the first wavelength, thereby causing absorption of the actinic radiation and decomposition of part of the superacid precursor, with formation of a protonated product derived from the dye. Thereafter, the medium is irradiated with actinic radiation of the second wavelength, thereby causing decomposition of part of the remaining superacid precursor, with formation of free superacid.

For the present process to occur, it is necessary that the sensitizing dye, having absorbed the radiation of the first wavelength, be capable of initiating the decomposition of the superacid precursor. As is well-known to those skilled in the art, for such initiation to occur, it is necessary to choose the sensitizing dye and the superacid precursor so that the excited state of the sensitizing dye is capable or reducing (or oxidizing) the superacid precursor. The choice of appropriate pairs of sensitizing dyes and superacid precursors may be made empirically, although techniques familiar to those skilled in the art, such as use of the Rehm-Weller Equation, may be used to reduce the amount of empirical testing necessary.

As already noted, in a preferred form of the process, only part of the medium is irradiated with the actinic radiation of the first wavelength but a larger portion of the medium is irradiated with the actinic radiation of the second wavelength, such that free superacid is generated in the part of the medium exposed to the radiation of both the first and second wavelengths, but no free superacid is generated in the part of the medium exposed to the radiation of the second wavelength but not to the radiation of the first wavelength. Desirably, the medium is imagewise exposed to the actinic radiation of the first wavelength so that the free superacid generated in the exposed areas of the medium forms a latent "image" in acid; this image is not necessarily visible to the unaided human eye but may be converted to a visible or otherwise useful image (e.g., a printing plate) as described below.

The superacid produced by the present process may be used to carry out any of the reactions which have hitherto been carried out using superacid generated by prior art processes. For example, the imaging medium may comprise a monomer or oligomer which polymerizes in the presence of the free superacid. If such a medium is imagewise exposed by the present process, in the part of the medium exposed to the radiation of both the first and second wavelengths, the monomer or oligomer polymerizes, but in the part of the medium not exposed to the radiation of the first wavelength, the monomer remains substantially unpolymerized. Alternatively, the imaging medium may comprise a polymer which depolymerizes in the presence of the free superacid. When such a medium is imagewise exposed by the present process, in the part of the medium exposed to the radiation of both the first and second wavelengths, the polymer depolymerizes, but in the part of the medium not exposed to the radiation of the first wavelength, the polymer remains substantially polymerized. The imaging medium may also comprise a polymer the solubility of which in a solvent changes in the presence of free superacid. Following exposure of the medium to the radiation of both the first and second wavelengths, the medium is treated with the solvent, whereby the polymer is removed from one of the exposed and unexposed areas of the medium (i.e., the areas of the medium exposed and not exposed respectively to the radiation of the first wavelength), but is not removed from the other of these areas. Thus, any of these types of imaging medium can act as a photoresist.

A further form of the present imaging medium comprises a polymer the adhesion of which to a material changes in the presence of the free superacid. Following exposure of the medium to the radiation of both the first and second wavelengths, the polymer is contacted with this material, so that one of the exposed and unexposed areas of the medium adheres to the material while the other of these areas does not adhere. For example, the present imaging medium may comprise a substrate in contact with one face of the layer(s) containing the imaging components (i.e., the superacid precursor, sensitizing dye and polymer), and a topcoat on the opposed side of the layer(s) containing the imaging components. The polymer is chosen (for example) so that before exposure to free superacid it adheres more strongly, whereas after exposure to free superacid it adheres less strongly to the substrate than to the topcoat. After imagewise exposure of the medium to the radiation of the first and second wavelengths, the substrate and topcoat are peeled away from one another. In unexposed areas, the polymer remains more adherent to the substrate than to the topcoat, and remains with the substrate, whereas in exposed areas, the polymer adheres less strongly to the substrate than to the topcoat, and consequently remains with the topcoat. Thus, upon peeling, the polymer-containing layer will fracture, with the unexposed parts remaining on the substrate and the exposed parts being removed with the topcoat.

Alternatively, the material with which the polymer is brought into contact after exposure can be a pulverulent material, for example a toning powder. An imaging medium of this type may comprise a polymer which is essentially non-tacky prior to exposure but which becomes tacky after exposure. After exposure, the toning powder is spread over the imaging medium, and adheres only to the exposed areas of polymer. Excess toning powder may then be removed, for example by blowing air across the imaging medium, thus leaving a visible image formed by the toning powder adhering only to the exposed areas of the imaging medium.

In another type of imaging medium of the present invention, the quantity of acid generated in the medium by the present process is increased ("amplified") by heating the medium, following the irradiation with the actinic radiation of the second wavelength, while the superacid is admixed with a secondary acid generator capable of superacid-catalyzed decomposition to form a second acid, the thermal decomposition of the acid generator being catalyzed by the presence of the superacid. When such an imaging medium is imagewise exposed to actinic radiation of the first wavelength, in the part of the medium irradiated with the actinic radiation of the first wavelength, the superacid catalyzes the decomposition of the secondary acid generator and the second acid is formed, whereas the part of the medium not irradiated with the actinic radiation of the first wavelength remains essentially free from the second acid.

The chemical changes which occur in exposed and unexposed regions of a preferred imaging medium of the present invention are shown in Table 1, below while the corresponding changes in acid concentration in exposed and unexposed areas are shown in FIGS. 1A-1D.

TABLE 1

| EXPOSED AREA | | UNEXPOSED AREA | |
|---|---|---|---|
| Component | Moles | Component | Moles |
| PRIOR TO EXPOSURE | | | |
| [DYE] | 1 | [DYE] | 1 |
| Secondary acid generator | 10 | Secondary acid generator | 10 |
| $Ph_2I^+PF_6^-$ | 5 | $Ph_2I^+PF_6^-$ | 5 |
| AFTER IMAGEWISE INFRA-RED EXPOSURE | | | |
| Ph-[DYE-H]$^+$PhIPF$_6^-$ | 0.75 | [DYE] | 1 |
| [DYE] | 0.25 | Secondary acid generator | 10 |
| Secondary acid generator | 10 | | 5 |
| $Ph_2I^+PF_6^-$ | 4.25 | $Ph_2I^+PF_6^-$ | |
| AFTER BLANKET ULTRA-VIOLET EXPOSURE | | | |
| Ph-[DYE-H]$^+$PhIPF$_6^-$ | 0.75 | [DYE] | 0.25 |
| [DYE-H]$^+$PF$_6^-$ | 0.25 | [DYE-H]$^+$PF$_6^-$ | 0.75 |
| HPF$_6$ | 0.5 | Secondary acid generator | 10 |
| Secondary acid generator | 10 | | |
| $Ph_2I^+PF_6^-$ | 3.5 | $Ph_2I^+PF_6^-$ | 4.25 |
| AFTER HEATING | | | |
| Ph-[DYE-H]$^+$PhIPF$_6^-$ | 0.75 | [DYE] | 0.25 |
| [DYE-H]$^+$PF$_6^-$ | 0.25 | [DYE-H]$^+$PF$_6^-$ | 0.75 |
| HPF$_6$ | 0.5 | Secondary acid generator | 10 |
| Secondary acid | 10 | | |
| $Ph_2I^+PF_6$ | 3.5 | $Ph_2I^+PF_6^-$ | 4.25 |
| AFTER BASE ADDITION | | | |
| Ph-[DYE-H]$^+$PhIPF$_6^-$ | 0.75 | [DYE] | 1 |
| [DYE-H]$^+$PF$_6^-$ | 0.25 | [BASE-H]$^+$PF$_6^-$ | 0.75 |
| [BASE-H]$^+$PF$_6^-$ | 0.5 | Secondary acid generator | 10 |
| Second acid | 9 | | |
| Base/second acid salt | 1 | $Ph_2I^+PF_6^-$ | 4.25 |
| $Ph_2I^+PF_6^-$ | 3.5 | | |

As shown in Table 1, prior to exposure both the exposed and unexposed regions comprise a quantity (shown in Table 1 as 1 mole for simplicity; all references to moles concerning Table 1 refer to moles per unit area of the imaging medium) of an infra-red sensitizing dye, a larger molar quantity of a superacid precursor (5 moles of $Ph_2I^+PF_6^-$ are shown in Table 1; a suitable quantity of a precursor sensitizer, such as pyrene, is also included in the medium but is not shown in Table 1) and a still larger molar quantity (10 moles are shown in Table 1) of a secondary acid generator.

The imaging medium is first imagewise irradiated with infra-red radiation of a frequency absorbed by the sensitizing dye, the amount of radiation applied being sufficient to cause the infra-red dye to bring about decomposition of less than one mole (0.75 mole is used for illustration in Table 1 and FIG. 1) of the superacid precursor. In the area of the imaging medium exposed to the infra-red radiation (hereinafter referred to as the "exposed area"), upon absorbing the infra-red radiation, the sensitizing dye transfers an electron to the superacid precursor, which then fragments to produce a phenyl radical and phenyl iodide. Although the secondary reactions which follow this fragmentation of the superacid precursor are not entirely understood at present, one pathway for further reaction may be combination of a radical cation derived from the sensitizing dye with the phenyl radical derived from the superacid precursor, and subsequent loss of a proton from the sensitizing dye to form a protonated species derived from the sensitizing dye and designated "Ph—[DYE—H]+" in Table 1, with charge balancing being effected by an anion derived from the superacid precursor. Each sensitizing dye molecule transfers only a single electron, and hence generates a single proton, before being converted to the protonated species, and this protonated species does not carry out the electron transfer reaction. Hence, since each sensitizing dye molecule brings about breakdown of only a single molecule of superacid precursor before being deactivated, the sensitizing dye will not bring about decomposition of a greater molar quantity of the superacid precursor than the molar quantity of sensitizing dye originally present, and the superacid generated is completely buffered by the dye. Hence, following the infra-red exposure, no free superacid is present in the exposed area. At this stage, the secondary acid generator in the exposed area remains unchanged. In the unexposed area, the infra-red irradiation effects no change in any of the components of the imaging medium.

The acid concentrations in the exposed and unexposed regions following this first step of the process are shown schematically in FIG. 1A, in which acid concentration is plotted along a line across the medium in which section BC is in an exposed area, while sections AB and CD are in unexposed areas. As shown in FIG. 2A, following the first step of the process, no acid is present in unexposed areas AB and CD, while the level of acid present in exposed area BC is below a threshold level T, which represents the level of acid which can be buffered by the sensitizing dye; theoretically, the level of acid in area BC should be 0.75T. Hence, as already stated, all of the acid present in exposed area BC is buffered by the sensitizing dye, and the imaging medium contains 0.75 mole of the Ph—[DYE—H]+ and no free superacid.

Figure 1B:
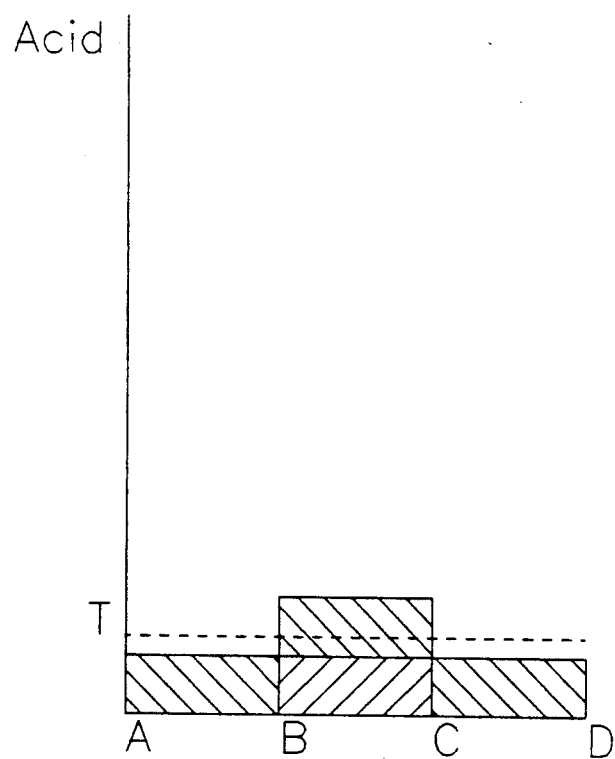

In the next stage of the imaging process, the whole of the imaging medium is irradiated with ultraviolet radiation effective to cause breakdown of the superacid precursor, with generation of free superacid. The amount of ultraviolet radiation irradiated is chosen so as to produce a molar amount of superacid less than the molar amount of dye present in the unexposed medium, and in Table 1 is shown as sufficient to produce 0.75 mole of superacid. As illustrated in Table 1 and FIG. 1B, in the exposed area BC of the imaging medium (i.e., in the area exposed to the infra-red radiation), the additional 0.75 mole of superacid generated by the ultra-violet exposure, combined with the 0.75 mole generated by the infra-red exposure, exceeds the threshold level T, and thus protonates all the sensitizing dye present and leaves additional superacid in free form. (For purposes of illustration, FIG. 1B shows the acid generated in the infra-red and ultra-violet exposures separately, although of course no difference exists chemically.) In the unexposed areas AB and CD, on the other hand, only the 0.75 mole of superacid generated by the ultra-violet exposure is present, the acid concentration remains below the threshold level T, and all of the superacid produced is buffered by the sensitizing dye, so that no free superacid is present following the ultra-violet irradiation. (As shown in Table 1, the buffered complex formed by the sensitizing dye and the superacid precursor in the unexposed areas AB and CD during the ultra-violet irradiation differs from that produced in the exposed area BC during the infra-red irradiation. During the ultraviolet irradiation, the superacid precursor typically transfers a phenyl group not to the dye but rather to the precursor sensitizer (which is effectively non-basic), so that only a proton comes to reside on the infra-red sensitizing dye. However, this difference between the two buffered complexes does not affect the present process, since both complexes efficiently buffer the superacid.)

Thus, at the end of the blanket ultraviolet irradiation, free superacid is present in the exposed area, whereas in the unexposed area no free superacid is present, all the superacid generated being buffered by the sensitizing dye.

The two steps already described may be the only steps of the present process. If, for example, the present process is to be used to bring about polymerization of a monomer or oligomer, or depolymerization of a polymer, the free superacid produced in area BC in FIG. 1B may be used directly to carry out the desired polymerization or depolymerization. It will be appreciated that, in such polymerization or depolymerization processes, the secondary acid generator can be omitted from the imaging medium.

Figure 1C:
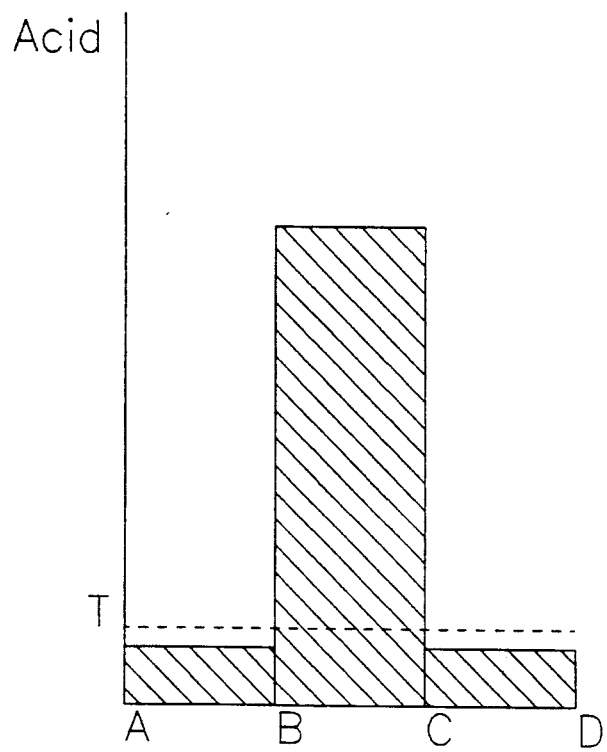
Figure 1D:
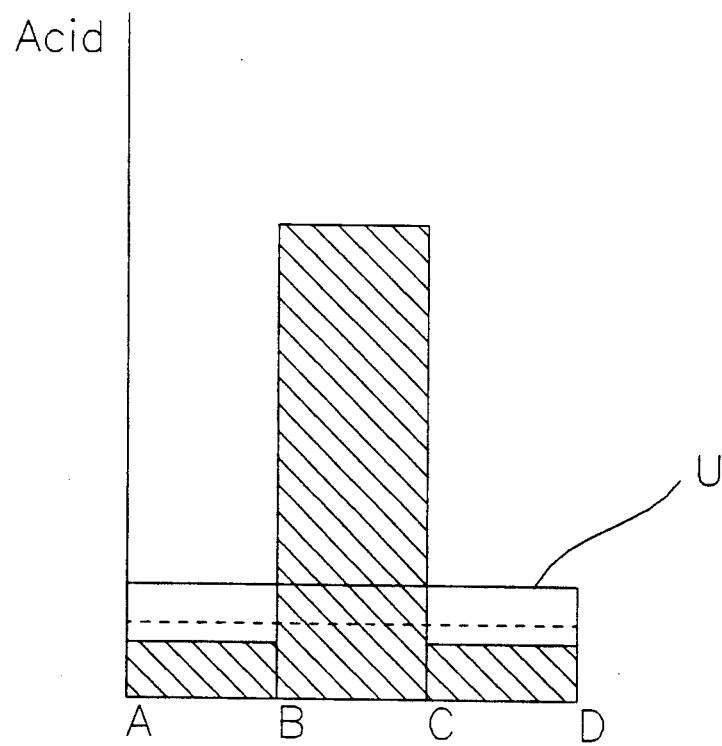

However, in a preferred process of the invention, the imaging medium is next heated. In the exposed area BC, the free superacid present catalyzes the decomposition of the secondary acid generator, thereby producing a large quantity of the second acid (10 moles are shown by way of example in Table 1; FIG. 1C is not strictly to scale). However, in the unexposed areas AB and CD, no free superacid is present, and the dye-superacid complex does not catalyze the decomposition of the secondary acid generator, so that essentially no decomposition of the secondary acid generator occurs and essentially no second acid is generated.

In the final step of the preferred process, as discussed in more detail below, a quantity of base is introduced into the imaging medium; 1.5 moles of base are shown in Table 1. The effect of this addition of base is to reduce acid levels throughout the imaging medium, as indicated by the box U in FIG. 1D. The addition of this base serves to ensure that, if a small amount of uncatalyzed thermal decomposition of the secondary acid generator does occur in unexposed areas AB and CD during the heating step, the small amount of second acid resulting will be neutralized by base before the second acid can effect changes in an acid-sensitive material, as described in more detail below. Although the addition of the base does reduce the amount of free acid present in the exposed area BC, this reduction is not significant since a more than adequate amount of second acid remains in the exposed area BC to affect an acid-sensitive material. The addition of base to the unexposed areas AB and CD leaves a surplus of base in these areas and thus serves to ensure that, if minor decomposition of the superacid precursor does occur after the present process has been completed, the minor amounts of superacid generated will be neutralized by the base and thus will not affect acid-sensitive material present in these unexposed areas.

From the foregoing description, it will be seen that, in the exposed area, the superacid catalyzes the breakdown of the secondary acid generator, so that the final quantity of second acid present is substantially larger than the quantity of superacid produced directly by the actinic radiation acting on the superacid precursor, although of course the secondary acid is typically a weaker acid than the superacid itself. This "chemical amplification" of the superacid by the secondary acid generator increases the number of moles of acid generated per einstein of radiation absorbed, and thus increases the contrast of the image produced by the present process as compared with simple generation of superacid by a superacid precursor. In practice, it has been found that, under proper conditions, at least 20 moles of second acid can be liberated for each mole of free superacid present in the exposed areas following the ultra-violet irradiation.

One of the advantages of the present process is that, at least in many preferred embodiments of the invention, it is possible to compensate for any premature breakdown of the superacid precursor which may occur prior to use of the imaging medium, for example as a result of exposure of the imaging medium to ambient infra-red or ultra-violet radiation during transportation and storage or because the combination of the superacid precursor and the sensitizing dye undergoes slow decomposition on protracted storage. With most infra-red sensitizing dyes, the protonated products derived from the sensitizing dye will absorb at a wavelength significantly different from the unprotonated sensitizing dye, so that it will be possible to differentiate between the unprotonated dye and protonated product by measuring absorption at an appropriate infra-red wavelength. The amount of infra-red and ultra-violet irradiation can be adjusted to ensure that the present process works properly even if some decomposition of the superacid precursor has taken place prior to use of the medium.

For example, to take an extreme case purely for purposes of illustration, suppose that the imaging medium shown in Table 1 is exposed to so much infra-red radiation during storage and transit that half of the infra-red sensitizing dye has already been converted to the Ph-[DYE-H]+ form prior to use, with corresponding breakdown of 0.5 mole of superacid precursor, so that in all areas the medium initially contains 0.5 mole of sensitizing dye, 10 moles of secondary acid generator, 4.5 moles of superacid precursor and 0.5 mole of Ph-[DYE-H]+. After infra-red analysis to determine the amount of Ph-[DYE-H]+, the infra-red irradiation may be adjusted so that, in exposed areas, only a further 0.4 mole of superacid precursor is decomposed by the dye. Thus, after the infra-red irradiation, the medium will contain 0.9 mole of the protonated product in exposed areas and 0.5 mole of the protonated product in unexposed areas.

If no change were made in the ultra-violet irradiation step described above with reference to Table 1, the results would be disastrous, since generation of a further 0.75 mole of acid in the unexposed areas would cause the acid concentration to exceed the threshold level, and the secondary acid generator would decompose in both the exposed and unexposed areas. Accordingly, based upon the results of the infra-red analysis, the ultra-violet irradiation is adjusted so that only (say) 0.4 mole of acid are decomposed in the exposed and unexposed areas. Accordingly, after the ultra-violet irradiation, the exposed areas contain 1.3 moles of acid (0.3 mole above threshold level) in the exposed areas and 0.9 mole (still below threshold level) in the unexposed areas. The slight reduction in the amount of free superacid in the exposed areas (0.3 mole, versus 0.5 mole in Table 1) will not significantly affect the results of the heating step, and the overall result of the imaging process will be unchanged.

For similar reasons, the present process is also relatively insensitive to variations in infra-red radiation, such as those caused by variations in laser output, variations between individual lasers in a laser diode array used to form the imaging beam, timing errors in laser drivers, etc. For example, in the process shown in Table 1, the infra-red irradiation causes decomposition of 0.75 mole of superacid precursor. If the infra-red radiation delivered to the imaging medium varies by ±20%, some exposed areas will experience decomposition of 0.6 mole of superacid precursor, while others will experience decomposition of 0.9 mole. After ultra-violet irradiation, the concentration of free superacid in the exposed areas will vary from 0.15 to 0.6 moles. In practice, with appropriate control of the heating step, this range of variation in free superacid concentration will have minimal effects on the final image.

Any of the known superacid precursors, for example diazonium, phosphonium, sulfonium and iodonium compounds, may be used in this invention, but iodonium compounds are preferred. Especially preferred superacid precurors are diphenyliodonium salts, specifically (4-octyloxyphenyl)phenyliodonium hexafluorophosphate and hexafluoroantimonate and bis(N-dodecylphenyl)iodonium hexafluoroantimonate.

Any infra-red dye capable of buffering the superacid employed may be used in the present process. Preferably, the infra-red dye is a squarylium dye, since squarylium dyes tend to have high infra-red extinction coefficients, have long singlet excited state lifetimes (which assists the electron transfer reactions upon which the present process depends), show little tendency to aggregate in polymeric films, and have low visible absorptions. Examples of infra-red dyes useful in the present process are:

a) dyes comprising an inner salt of a compound of the formula:

$$Q^1\!=\!Z\!-\!Q^2$$

wherein:
Q$^1$ is a 4-(benz[b]-4H-pyrylium)methylidene, 4-(benz[b]-4H-thiopyrylium)methylidene or 4-(benz[b]-4H-selenopyrylium)methylidene grouping;

Z is a 1,3-(2-hydroxy-4-oxo-2-cyclobutylidene) hydroxide or 1,3-(2-hydroxy-4,5-dioxo-2-cyclopentylidene) hydroxide ring; and Q$^2$ is a 4-(benz[b]-4H-pyran-4-ylidene)methyl, 4-(benz[b]-4H-thiopyran-4-ylidene)methyl or 4-

(benz[b]-4H-selenopyran-4-ylidene)methyl grouping;

wherein at least one of the groupings $Q^1$ and $Q^2$ carries at its 2-position a substituent in which a non-aromatic carbon atom is bonded directly to the benzpyrylium, benzthiopyrylium or benzeselenopyrylium nucleus, subject to the proviso that if said 2-substituent contains an aromatic nucleus, this aromatic nucleus is not conjugated with the benzpyrylium, benzthiopyrylium or benzselenopyrylium nucleus to which it is attached (see U.S. application Ser. No. 07/795,038, filed Nov. 20, 1991 in the names of Stephen J. Telfer et al., and assigned to the same assignee as the present application);

b) squarylium compounds of the formula:

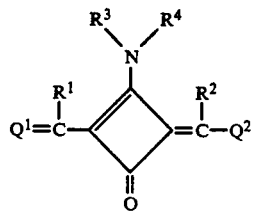

in which $Q^1$ and $Q^2$ are each a chromophoric group having an unsaturated system conjugated with the squarylium ring and such that in the compounds of formulae $Q^1CH_2R^1$ and $Q^2CH_2R^2$ the methylene hydrogens are active hydrogens, $R^1$ and $R^2$ are each independently a hydrogen atom or an aliphatic or cycloaliphatic group, and $R^3$ and $R^4$ are each independently a hydrogen atom, or an aliphatic, cycloaliphatic, aromatic or heterocyclic group, or one of $R^3$ and $R^4$ is a hydrogen atom and the other is an organosulfonyl group, or $R^3$ and $R^4$ together with the intervening nitrogen atom form a cycloaliphatic or aromatic ring (see U.S. Pat. No. 5,227,498); and c) squarylium compounds of the formula:

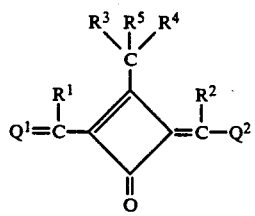

in which:

$Q^1$ and $Q^2$ are each a chromophoric group having an unsaturated system conjugated with the squarylium ring and such that in the compounds of formulae $Q^1CH_2R^1$ and $Q^2CH_2R^2$ the methylene hydrogens are active hydrogens;

$R^1$ and $R^2$ are each independently a hydrogen atom or an aliphatic or cycloaliphatic group; and $R^3$, $R^4$ and $R^5$ are each independently a hydrogen atom, or an aliphatic, cycloaliphatic, aromatic or heterocyclic group, or an electron-withdrawing group able to lower the electron density at the carbon atom to which it is attached, subject to the provisoes that:

two of $R^3$, $R^4$ and $R^5$ may form a divalent group of which a single atom is double bonded to the carbon atom to which the two groups are attached, or all three of $R^3$, $R^4$ and $R^5$ may form a trivalent group of which a single atom is triple bonded to the carbon atom to which the three groups are attached, or two of $R^3$, $R^4$ and $R^5$ may, together with the carbon atom to which they are attached, form a ring, or all three of $R^3$, $R^4$ and $R^5$ may, together with the carbon atom to which they are attached, form an unsaturated ring (see U.S. Pat. No. 5,227,499).

Any secondary acid generator which is capable of superacid-catalyzed breakdown to give a second acid may be used in the present process. Preferred secondary acid generators are 3,4-disubstituted-cyclobut-3-ene-1,2-diones (hereinafter for convenience referred to as "squaric acid derivatives") capable of generating squaric acid or an acidic derivative thereof, since squaric acid and its acidic derivatives are strong acids well suited to effecting color changes or other effects (for example, polymerization or depolymerizations reactions) in acid-sensitive materials. Especially preferred squaric acid derivatives are those in which there is bonded to the squaric acid ring, via an oxygen atom, an alkyl or alkylene group, a partially hydrogenated aryl or arylene group, or an aralkyl group. The acid-catalyzed decomposition of these squaric acid derivatives causes replacement of the original alkoxy, alkyleneoxy, aryloxy, aryleneoxy or aralkoxy group of the derivative with a hydroxyl group, thereby producing squaric acid or an acidic squaric acid derivative having one hydroxyl group.

The exact mechanism by which squaric acid or an acidic derivative thereof is formed in the present process may vary depending upon the type of squaric acid derivative employed. In some cases, for example di-t-butyl squarate, one or both groups attached via oxygen atoms to the squaric acid ring may thermally decompose to yield an alkene or arene, thereby converting an alkoxy or aryloxy group to a hydroxyl group and forming the squaric acid or acidic derivative thereof. In other cases, for example 3-amino-4-(p-vinylbenzyloxy)-cyclobut-3-ene-1,2-dione, there is no obvious mechanism for formation of a corresponding alkene or arene, and it appears that the mechanism of acid formation is migration of the vinylbenzyl or similar group to a different position within the molecule (probably to the amino group), and protonation of the remaining oxygen atom to form a hydroxyl group at the position from which the group migrates. In other cases, neither of these pathways is possible. However, in all cases the net effect is the replacement of the alkoxy, alkyleneoxy, aryloxy, aryleneoxy or aralkoxy group present in the original derivative with a hydroxyl group to form squaric acid or an acidic derivative thereof.

There are four preferred groups of squaric acid derivatives for use in the present process:

(a) those of the formula:

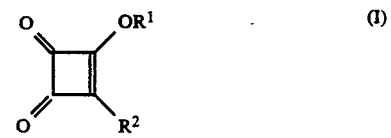

in which $R^1$ is an alkyl group, a partially hydrogenated aromatic group, or an aralkyl group, and $R^2$ is a hydrogen atom or an alkyl, cycloalkyl, aralkyl, aryl, amino, alkylamino, dialkylamino, alkylthio, alkylseleno, dialkylphosphino, dialkylphosphoxy or trialkylsilyl group, subject to the proviso that either or both of the groups $R^1$ and $R^2$ may be attached to a polymer. Among the derivatives of Formula I, especially preferred groups are those in which (a) $R^1$ is an unsubstituted or phenyl substituted alkyl group containing a total of not more than about 20 carbon atoms in which the carbon atom directly bonded to the oxygen atom has not more than one hydrogen atom attached thereto, and $R^2$ is an alkyl group containing not more than about 20 carbon atoms, or a phenyl group (which may be substituted or unsubstituted); and (b) $R^1$ is a benzyloxy group and $R^2$ is an amino group.

(b) those of the formula:

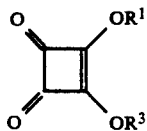

(II)

in which $R^1$ and $R^3$ independently are each an alkyl group, a partially hydrogenated aryl group or an aralkyl group, subject to the proviso that either or both of the groups $R^1$ and $R^3$ may be attached to a polymer. Among the derivatives of Formula II, an especially preferred group are those in which $R^1$ and $R^3$ are each independently an unsubstituted or phenyl substituted alkyl group containing a total of not more than about 20 carbon atoms in which the carbon atom directly bonded to the oxygen atom has not more than one hydrogen atom attached thereto. Specific preferred compounds of Formula II are those in which $R^1$ and $R^3$ are each a tertiary butyl group, an α-methylbenzyl group or a cyclohexyl group, namely di-tertiary butyl squarate, bis(α-methylbenzyl) squarate and dicyclohexyl squarate.

(c) those of the formula:

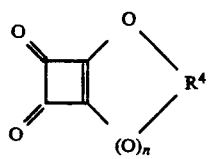

(III)

in which n is 0 or 1, and $R^4$ is an alkylene group or a partially hydrogenated arylene group. Among the derivatives of Formula III, an especially preferred group are those in which n is 1 and $R^4$ is an alkylene group containing not more than about 12 carbon atoms, in which each of the carbon atoms directly bonded to the oxygen atoms has not more than one hydrogen atom attached thereto.

(d) those having at least one unit of the formula:

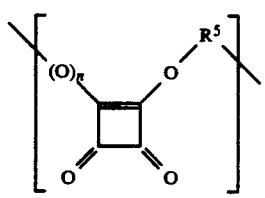

(IV)

in which n is 0 or 1, $R^5$ is an alkylene or partially hydrogenated arylene group. In addition to the fragmentable groups $R^5$, the compounds may also contain one or more units in which a non-fragmentable group is attached to a squarate ring, directly or via an oxygen atom.

The squaric acid derivatives of Formula IV include not only high polymers, but also dimers, trimers, tetramers, etc. including at least one of the specified units. The terminating groups on the derivatives of Formula IV may be any of groups $OR^1$ or $R^2$ discussed above with reference to Formula I. Thus, for example, Formula IV includes the squaric acid dimer derivative of the formula:

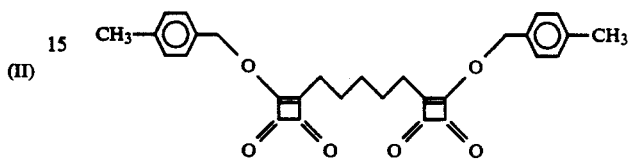

The squaric acid derivatives of Formulae I and II are usually monomeric. However, these derivatives of Formulae I and II can be incorporated into polymers by having at least one of the groups $R^1$, $R^2$ and $R^3$ attached to a polymer. Attachment of the squaric acid derivatives to a polymer in this manner may be advantageous in that it may avoid incompatibility and/or phase separation which might occur between a monomeric squaric acid derivative of Formula I or II and a polymeric binder needed in an imaging medium.

The attachment of the groups $R^1$, $R^2$ and $R^3$ to a polymer may be effected in various ways, which will be familiar to those skilled in the art of polymer synthesis. The squaric acid derivatives may be incorporated into the backbone of a polymer; for example, the groups may contain unsaturated linkages which enable the squaric acid derivatives to be polymerized either alone or in admixture with other unsaturated monomers. Alternatively, the squaric acid derivatives may be added as sidechains to a polymer; for example, one of the groups $R^1$, $R^2$ and $R^3$ could contain an amino group able to react with a polymer containing a carboxyl groups or derivatives thereof to form an amide linkage which would link the squaric acid derivative as a sidechain on to the polymer.

In the present process, it is generally undesirable to form substantial quantities of gas during the superacid-catalyzed decomposition of the squaric acid derivative since such gas may distort the medium containing the squaric acid derivative or form vesicles therein, and such distortion or vesicle formation may interfere with proper image formation. Accordingly, if the decomposition of the squaric acid derivative yields an alkene, it is desirable that the groups $R^1$, $R^3$, $R^4$ and $R^5$ be chosen so that this alkene is a liquid at 20° C., and preferably higher, since some heating of the alkane will inevitably occur during the superacid-catalyzed decomposition. In some cases, however, the alkane liberated may be sufficiently soluble in the medium containing the squaric acid derivative that liberation of a highly volatile alkane will not result in distortion of, or vesicle formation in, the medium.

As already mentioned, the present process may be used for various purposes, such as triggering of an acid-catalyzed chemical reaction (for example, polymerization or depolymerization reactions). When the present process is used for image formation, simultaneously with or subsequent to the heating step, the second acid is contacted with an acid-sensitive material which changes color in the presence of the second acid. (It will be appreciated that the "color change" involved in such an imaging process need not be a visible color change. If, for example, the present process is used to provide security markings intended to be machine-readable, the "color change" could be a change in absorption from one non-visible wavelength to another, such that it can be detected by the appropriate machine-reading device.)

The acid-sensitive material used in the process of the present invention may be any material which undergoes a color change in the presence of the second acid. Thus any conventional indicator dye may be used as the acid-sensitive material, as may be leuco dyes disclosed in the aforementioned U.S. Pat. Nos. 4,602,263; 4,720,449 and 4,826,976, which are also sensitive to acid.

The exposure of the medium to the actinic (typically infra-red) radiation of the first wavelength can be effected in any of the ways conventionally used for exposing media to the same type of radiation. In some cases, it may be convenient to employ a laser of the appropriate wavelength, since the use of a laser is a convenient way to record data as an image pattern in response to transmitted signals, such as digitized information.

Some imaging media of the present invention (for example those intended for use as photoresists and containing polymerizable monomers or oligomers or depolymerizable polymers) may comprise only a single layer containing all the components of the imaging medium. However, media containing a secondary acid generator and an acid-sensitive material desirably comprise two separate layers or phases, so that, prior to the heating, the acid-sensitive material is present in a layer or phase separate from the layer or phase containing the superacid precursor and the secondary acid generator, and following the generation of the second acid from the secondary acid generator, the two layers or phases are mixed, thereby effecting the color or other change in the acid-sensitive material.

It should be noted that, although in principle the mixing of the acid-sensitive material the superacid precursor, sensitizing dye and secondary acid generator should be effected after the generation of the second acid from the secondary acid generator, in practice if the superacid precursor, sensitizing dye and secondary acid generator are present in one layer of a two-layer imaging medium, and the acid-sensitive material in the other layer of the medium, these two layers being such that they mix on heating, both the generation of the second acid and the mixing of the two layers may be effected in a single heating step, since the superacid-catalyzed decomposition of the secondary acid generator will typically be essentially complete before mixing of the two layers becomes significant.

When a two-layer structure is used, it is not necessary that the two layers be affixed to one another before imaging. The production of unbuffered superacid and second acid in exposed regions effected by the present processes are "permanent" chemical changes, and hence it is possible to delay contacting the exposed medium with an acid-sensitive material for a substantial time. (Obviously, excessive delay may reduce the quality of an image produced by allowing superacid or second acid to diffuse from exposed into unexposed areas of the medium.) Accordingly, the two layers of the imaging medium may be laminated together after the second irradiation. However, in general it is most convenient to form the two layers by coating one on the other, or laminating the two layers together before imaging, since in this way only a single sheet of material has to handled during the imaging process. Since it is important that the two layers not mix prematurely, if the two layers are to be coated successively on to a support, it is usually desirable to coat one layer from an aqueous medium and the other from a non-aqueous medium. Typically, the layer containing the superacid precursor is coated from an organic solution and the layer containing an acid-sensitive leuco dye or other material is coated from an aqueous dispersion.

As already mentioned above with reference to Table 1 and FIG. 1, prior to the heating step, the acid-sensitive material may be in admixture with an amount of a basic material insufficient to neutralize all the second acid liberated by the secondary acid generator during the heating, so that the second acid liberated by the secondary acid generator during the heating neutralizes all of the basic material and leaves excess second acid sufficient to effect the change in the acid-sensitive material. The provision of this basic material serves to "soak up" minor amounts of acid which may be generated in unexposed areas after exposure due, for example, to slow decomposition of the superacid precursor/sensitizing dye mixture during protracted storage. Since obviously the basic material cannot be allowed to contact the superacid present after the second irradiation but prior to the heating step, desirably the acid-sensitive material is present in a layer or phase separate from the layer or phase containing the superacid precursor and the secondary acid generator and, following the generation of the second acid, the two layers or phases are mixed, thereby effecting the change in the acid-sensitive material.

In addition to the two aforementioned layers or phases containing the superacid precursor, sensitizing dye, secondary acid generator and acid-sensitive material, the imaging media of the present invention may comprise a support and additional layers, for example, a subbing layer to improve adhesion to the support, acid-impermeable interlayers fro separating multiple imaging layers from one another, an anti-abrasive topcoat layer, and other auxiliary layers.

The support employed may be transparent or opaque and may be any material that retains its dimensional stability at the temperature used for image formation. Suitable supports include paper, paper coated with a resin or pigment, such as, calcium carbonate or calcined clay, synthetic papers or plastic films, such as polyethylene, polypropylene, polycarbonate, cellulose acetate and polystyrene. The preferred material for the support is a polyester, desirably poly(ethylene terephthalate).

Usually the layers containing the superacid precursor, sensitizing dye, secondary acid generator and acid-sensitive material will also contain a binder; typically these layers are formed by combining the active materials and the binder in a common solvent, applying a layer of the coating composition to the support and then drying. Rather than a solution coating, the layer may be applied as a dispersion or an emulsion. The coating composition also may contain dispersing agents, plasticizers, defoaming agents, coating aids and materials such as waxes to prevent sticking.

The binder used for the layer(s) in which superacid is to be generated must of course be non-basic, such that the superacid is not buffered by the binder. Examples of binders that may be used include styrene-acrylonitrile copolymers, polystyrene, poly(α-methylstyrene), copolymers of styrene and butadiene, poly(methyl methacrylate), copolymers of methyl and ethyl acrylate, poly(vinyl butyral), polycarbonate, poly(vinylidene chloride) and poly(vinyl chloride). It will be appreciated that the binder selected should not have any adverse effect on the superacid precursor, sensitizing dye, secondary acid generator or the acid-sensitive material incorporated therein. Also, the binder should be heat-stable at the temperatures encountered during the heating step and should be transparent so that it does not interfere with viewing of the image. The binder must of course transmit the actinic radiation used in the exposure steps.

The squaric acid derivatives preferably used as acid generators in the process of the present invention can be prepared by known methods, such as those described in U.S. Pat. No. 4,092,146 and Tetrahedron Letters (1977), 4437–38, and 23, 361–4, and Chem. Ber. 121, 569–71 (1988) and 113, 1–8 (1980). In general, the diesters of Formula II can be prepared by reacting disilver squarate with the appropriate alkyl halide(s), preferably the alkyl bromides. The ester groupings may be varied by routine transesterification reactions, or by reacting the diacid chloride of squaric acid with an appropriate alkoxide.

Figure 2:
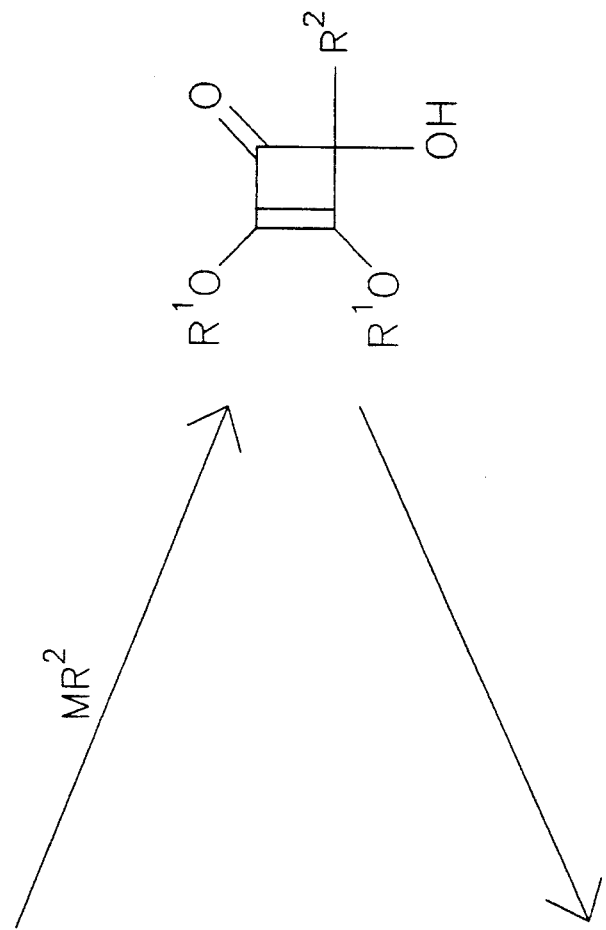
FIG. 2 shows a synthesis of a squaric acid derivative of Formula I below.
Figure 2:
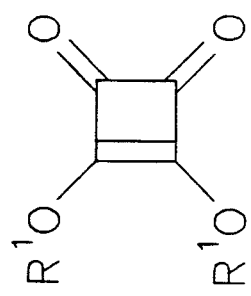
Figure 2:
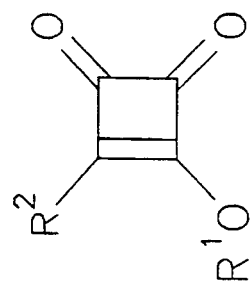

The derivatives of Formula I in which $R^2$ is an alkyl, cycloalkyl, aralkyl or aryl group can be prepared from derivatives of Formula II by the synthesis shown in FIG. 2. The diester of Formula II is first condensed with a compound containing a negatively charged species $R^2$; this compound is normally an organometallic compound, and preferably an organolithium compound. The reaction adds the —$R^2$ group to one of the oxo groups of the diester to produce the squaric acid derivative of Formula VI; to avoid disubstitution into both oxo groups, not more than the stoichiometric amount of the organometallic reagent should be used.

After being separated from unreacted starting material and other by-products, the squaric acid derivative VI is treated with an acid, for example hydrochloric acid, to convert it to the desired squaric acid derivative I. Although it is possible to simply add acid to the reaction mixture resulting from the treatment of the diester with the organometallic reagent, this course is not recommended, since the squaric acid derivative I produced may be contaminated with unreacted diester, and the diester and squaric acid derivative I are so similar that it is extremely difficult to separate them, even by chromatography.

It will be appreciated that the synthesis shown in FIG. 2 may be modified in various ways. If, for example, the nature of the group $R^1$ desired in the final compound of Formula I is such that it would react with the organometallic reagent, the reactions shown in FIG. 2 may be carried out with a diester in which the ester groupings do not contain the group $R^1$, and the final product of Formula I may be subjected to transesterification or other reactions to introduce the group $R^1$.

The derivatives of Formula I in which $R^2$ is an amino, alkylamino or dialkylamino group can be prepared by similar methods from squaric acid diesters. For example, as illustrated in the Examples below, reaction of bis(4-vinylbenzyl) squarate with methylamine gives 3-amino-4-(p-vinylbenzyloxy)cyclobut-3-ene-1,2-dione. Analogous methods for the synthesis of the other compounds of Formula I will readily be apparent to those skilled in the art of organic synthesis.

The forms of the squaric acid derivatives of Formulae I and II in which at least one of $R^1$, $R^2$ and $R^3$ is attached to a polymer may be prepared by reactions analogous to those used to prepare the monomeric derivatives of Formulae I and II, for example by treating a polymer containing appropriate alkoxide groups with the diacid chloride or a monoester monoacid chloride of squaric acid. Alternatively, these polymer-attached derivatives may be prepared by transesterification, for example by treating a polymer containing esterified hydroxyl groups with a monomeric squaric acid derivative of Formula I or II. Other methods for attachment of these derivatives to polymers, or inclusion of these derivatives into polymer backbones, have already been discussed above.

The derivatives of Formula III may be prepared by transesterification from derivatives of Formula II, or another squaric acid diester, and the appropriate diol.

A preferred embodiment of the invention will now be described, though by way of illustration only, with reference to FIG. 3 of the accompanying drawings, which shows a schematic cross-section through an imaging medium (generally designated 10) of the invention as the image therein is being fixed by being passed between a pair of hot rollers 12.

The imaging medium 10 comprises a support 14 formed from a plastic film. Typically the support 14 will comprise a polyethylene terephthalate film 3 to 10 mils (76 to 254 mμ) in thickness, and its upper surface (in FIG. 3) may be treated with a sub-coat, such as are well-known to those skilled in the preparation of imaging media, to improve adhesion of the other layers to the support.

On the support 14 is disposed an acid-generating layer 16 comprising a superacid precursor, an infra-red sensitizing dye and a secondary acid generator, which undergoes a superacid-catalyzed thermal decomposition to form a second acid. On the opposed side of the acid-generating layer 16 from the support 14 is disposed a color-forming layer 18 comprising an acid-sensitive material, which changes color in the presence of an acid, and a small amount of a base. The acid-generating layer 16 and the imaging layer 18 both contain a binder having a glass transition temperature substantially above room temperature.

Finally, the imaging medium comprises an abrasion-resistant topcoat 20.

The imaging medium 10 may be formed by coating the layers 16, 18 and 20 on to the support 14. Alternatively, for example, the layers 16 and 18 may be coated on to the support 14, and the topcoat 20 laminated on to the resultant structure.

The imaging medium 10 is exposed by writing on selected areas of the medium with an infra-red laser, this exposure being effected through the support 14, as indicated by the arrow 22 in the drawing (alternatively, exposure could be effected through the topcoat 20). Within the exposed regions of the acid-generating layer 16, the exposure to infra-red radiation causes breakdown of the superacid precursor with the formation of the corresponding superacid buffered by the sensitizing dye, as described above. After this infra-red exposure, the imaging medium 10 is passed beneath a mercury lamp and given a blanket ultraviolet exposure to produce free superacid in the infra-red exposed areas, and then passed between the heated rollers 12. The heat applied by the rollers 12 causes the superacid present in the exposed regions of the acid-generating layer 16 to cause catalytic breakdown of the secondary acid generator therein, thereby causing formation of a quantity of second acid substantially larger than the quantity of superacid originally generated by the ultra-violet radiation. The heat and pressure applied by the rollers 12 also raise the color-forming layer 18 and the acid-generating layer 16 above their glass transition temperatures, thereby causing the components dispersed in these two layers to become intermixed so that, in exposed regions, the second acid produced in the acid-generating layer 16 effects the color change of the acid-sensitive material, thereby forming an image.

The imaging medium 10 shown in FIG. 3 will produce monochrome images. As will readily be apparent to those skilled in the imaging art, this imaging medium 10 may readily be modified to produce full color images by including two or more additional pairs of color-forming layers 18 and acid-generating layers 16, with acid-impermeable interlayers provided between each adjacent pair of layers, the interlayers having a glass transition temperature sufficiently high that it is not exceeded during passage of the medium between the rollers 12, so that the interlayers prevent mixing of adjacent pairs of layers 16 and 18. Typically, a multicolor medium will comprise three pairs of color-forming layers 18 and acid-generating layers 16 arranged to produce yellow, cyan and magenta images, as in conventional multicolor imaging media. The acid-generating layers 16 in such a medium will contain infra-red sensitizing dyes absorbing at differing wavelengths so that the three color-forming layers can be imaged independently of one another using three infra-red lasers of differing wavelengths. It should be noted that only the infra-red sensitizing dyes need differ among the plurality of acid-generating layers; conveniently, all the acid-generating layers can make use of the same superacid precursor and secondary acid generator.

The following Examples are now given, though by way of illustration only, to show details of preferred reagents, conditions and techniques used in the process and imaging medium of the present invention.

3,4-Bis(benzyloxy)cyclobut-3-en-1,2-dione ("dibenzyl squarate") used in Examples 11 and 12 below was prepared as described in N. Islam et al, Tetrahedron 43, 959-970 (1987).

EXAMPLE 1

Preparation of bis(3-bromo-2,3-dimethylbut-2-yl) squarate

This Example illustrates the preparation of 3,4-bis(3-bromo-2,3-dimethylbut-2-oxy)-cyclobut-3-ene-1,2-dione ("bis(3-bromo-2,3-dimethylbut-2-yl) squarate"), the compound of Formula II in which $R^1$ and $R^3$ are each a 3-bromo-2,3-dimethylbut-2-yl group.

Silver squarate (1.0 g, 3.0 mmol) was added to a solution of 2,3-dibromo-2,3-dimethylbutane (1.0 g, 4.0 mmol) in dry ether (3 mL) at room temperature. The suspension became warm, and was cooled by a water bath at room temperature. After six hours' stirring, the precipitate remaining was removed by filtration, and washed with ether. The combined ether extracts were concentrated, and the crude product obtained therefrom was purified by flash chromatography on silica gel with 1:3 ether/hexanes as eluent to give the diester (140 mg, 11% yield) as a white powder which decomposed at 131°-132° C. The structure of the compound was confirmed by mass spectroscopy and by $^1H$ and $^{13}C$ NMR spectroscopy.

EXAMPLE 2

Preparation of 3-t-butoxy-4-phenylcyclobut-3-ene-1,2-dione

This Example illustrates the preparation of 3-t-butoxy-4-phenylcyclobut-3-ene-1,2-dione, the compound of Formula I in which $R^1$ is a tertiary butyl group and $R^2$ is a phenyl group.

Phenyl magnesium bromide (4.6 mL of a 1.0M solution in THF, 4.6 mmol) was added dropwise over a period of 5 minutes to a solution of di-t-butyl squarate (1.0 g, 4.42 mmol) in dry ether (10 mL) at −78° C. under nitrogen. After 30 minutes, the reaction mixture was warmed to 0° C., and stirred at this temperature for an additional one hour. Water (10 mL) and ether (10 mL) were then added to the reaction mixture and the layers were separated. The aqueous layer was extracted twice with dichloromethane. The combined organic layers were dried over magnesium sulfate and concentrated, to give a yellow oil (1.43 g), which crystallized. The resultant material was dissolved in dichloromethane (25 mL) and concentrated hydrochloric acid (4 drops) was added, with stirring, to this solution at room temperature. After 30 minutes, a further four drops of concentrated hydrochloric acid were added. Dichloromethane (25 mL) was added, and the resultant solution was washed with a saturated solution of sodium bicarbonate and then with brine, dried over magnesium sulfate, and concentrated. The crude product thus obtained was purified by flash chromatography on silica gel with toluene as eluent. The chromatographed material was further purified by recrystallization from toluene/hexanes to give the desired monoester as yellow crystals (142 mg, 14% yield) which decomposed at 105°-110° C. The structure of this compound was confirmed by mass spectroscopy and by $^1H$ and $^{13}C$ NMR spectroscopy.

EXAMPLE 3

Preparation of 3,4-bis(α-methylbenzyloxy)-cyclobut-3-ene-1,2-dione

This Example illustrates the preparation of 3,4-bis(α-methylbenzyloxy)-cyclobut-3-ene-1,2-dione ("bis(α-methylbenzyl) squarate"), the compound of Formula II in which $R^1$ and $R^3$ are each an α-methylbenzyl group.

1-Bromo-1-phenylethane (3.1 g, 16.8 mmol) was added dropwise to a suspension of silver squarate (2.5 g, 7.62 mmol, prepared as described in S. Cohen et al., J. Am. Chem. Soc., 88, 5433 (1966)) in dry ether (40 mL) at 0° C. After the addition was complete, the reaction mixture was allowed to warm to room temperature and was stirred for four hours in the dark. The solid remaining after this time (silver bromide) was removed by filtration and washed with more ether. The combined ether solutions were washed with a saturated solution of sodium bicarbonate and dried over sodium sulfate. Evaporation of the solvent was followed by purification by flash chromatography on silica gel with 0–60% ether/hexanes as eluant to give the desired diester (394 mg, 16% yield) as a colorless oil. The diester was obtained as a mixture of diastereoisomers which were not separable by this type of chromatography. The structure of the diester was confirmed by mass spectroscopy and by $^1H$ and $^{13}C$ NMR spectroscopy.

EXAMPLE 4

Preparation of 3,4-bis(p-methylbenzyloxy)-cyclobut-3-ene-1,2-dione

This Example illustrates the preparation of 3,4-bis(p-methylbenzyloxy)-cyclobut-3-ene-1,2-dione ("bis(p-methylbenzyl) squarate"), the compound of Formula II in which $R^1$ and $R^3$ are each a p-methylbenzyl group.

Triethylamine (0.93 g, 9.2 mmol) was added to a stirred suspension of squaric acid (0.5 g, 4.38 mmol) in chloroform (10 mL) and the resultant solution was cooled with an ice/water bath. A solution of α-bromo-p-xylene (2.03 g, 11.0 mmol) in chloroform (10 mL) was then added dropwise over a period of 30 minutes. After this time, the cooling bath was removed and the solution was held at room temperature for 4.5 hours. The reaction mixture was then diluted with chloroform (20 mL), washed successively with a saturated aqueous solution of sodium bicarbonate (2×20 mL) and saturated brine (20 mL), dried over magnesium sulfate and concentrated under reduced pressure. The resultant oil was further purified by partition between ether (50 mL) and saturated aqueous sodium bicarbonate (20 mL) and separation of the organic layer. The organic layer was washed successively with a saturated aqueous solution of sodium bicarbonate (20 mL) and saturated brine (20 mL), dried over magnesium sulfate and concentrated under reduced pressure. The oil which resulted was crystallized from hot hexanes (20 mL) to give the desired compound (300 mg, 21.3% yield) as off-white crystals. The structure of this compound was confirmed by mass spectroscopy and by $^1H$ and $^{13}C$ NMR spectroscopy.

EXAMPLE 5

Preparation of 3,4-bis(cyclohexyloxy)-cyclobut-3-ene-1,2-dione

This Example illustrates the preparation of 3,4-bis(cyclohexyloxy)cyclobut-3-ene-1,2-dione ("dicyclohexyl squarate"), the compound of Formula II in which $R^1$ and $R^3$ are each a cyclohexyl group.

Cyclohexyl bromide (9.95 g, 61 mmol) was added dropwise over a period of 20 minutes to a stirred suspension of silver squarate (4.0 g, 12.2 mmol, prepared as described in S. Cohen et al., J. Am. Chem. Soc., 88, 5433 (1966)) in ether (80 mL) in the dark with ice/water cooling. The ice bath was then removed and the reaction mixture was stirred overnight at room temperature, then filtered to remove silver bromide, and the residue was washed with ether (2×20 mL). The ether solutions were combined and washed successively with a saturated aqueous solution of sodium bicarbonate (50 mL) and saturated brine (50 mL), dried over magnesium sulfate and concentrated under reduced pressure to give the desired compound as a viscous oil which solidified upon storage in a refrigerator to give an off-white solid (0.55 g, 16% yield). The structure of this compound was confirmed by mass spectroscopy and by $^1H$ and $^{13}C$ NMR spectroscopy.

EXAMPLE 6

Preparation of 3-amino-4-(t-butoxy)-cyclobut-3-ene-1,2-dione

This Example illustrates the preparation of 3-amino-4-(t-butoxy)cyclobut-3-ene-1,2-dione, the compound of Formula I in which $R^1$ is a tertiary butyl group and $R^2$ is an amino group.

A stream of ammonia gas was passed into a stirred solution of Compound A (0.7 g, 3.07 mmol) in methanol (40 mL) for 2 minutes. The solution was then allowed to stand at room temperature for 1 hour, during which time a small amount of insoluble material was precipitated. The sediment was removed by filtration, and the solvent was removed under reduced pressure to yield a yellow solid, which was washed with ether (2×50 mL) to remove starting material and butanol (0.16 g of impurities were collected, after solvent evaporation). The solid which remained was dissolved in dichloromethane (150 mL) and the solution was filtered. Removal of the solvent under reduced pressure yielded the desired compound as white crystals (0.25 g, 48% yield) which melted at 220°-225° C. The structure of this compound was confirmed by $^1H$ NMR spectroscopy.

EXAMPLE 7

Preparation of 4-hexyl-3-(p-vinyl-benzyloxy)cyclobut-3-ene-1,2-dione

This Example illustrates the preparation of 4-hexyl-3-(p-vinylbenzyloxy)-cyclobut-3-ene-1,2-dione, the compound of Formula I in which $R^2$ is a hexyl group and $R^1$ is an p-vinylbenzyl group.

Part A: Preparation of 2,3-dibutoxy-4-hexyl-4-hydroxycyclobut-2-en-1-one

Hexyl magnesium bromide (40 mL of a 2M solution in ether, 80.0 mmol) was added dropwise over a period of 45 minutes to a solution of di-n-butyl squarate in dry THF (150 mL) at −78° C. under nitrogen, and the reaction mixture was held at that temperature for 1 hour. The reaction mixture was then allowed to warm to room temperature are stirred for an additional 3 hours, after which time it was cooled using an ice/water bath, and quenched by the addition of water (25 mL) added dropwise over a period of 5 minutes. Saturated brine (300 mL) and ether (300 mL) were then added, the layers were separated, and the aqueous layer was extracted with additional ether (300 mL). The ether extracts were combined and dried over magnesium sulfate, and the solvents were removed to give a golden oil (15.64 g) containing the desired product; this oil was used without further purification in Part B below.

Part B: Preparation of 3-hexyl-4-hydroxy-cyclobut-3-en-1,2-one

6N Hydrochloric acid (150 mL) was added in portion to a stirred solution of crude 2,3-dibutoxy-4-hexyl-4-hydroxycyclobut-2-en-1-one (15.1 g, prepared in Part A above) in THF (150 mL), and the resultant solution was stirred at room temperature for 3 hours. The reaction mixture was then concentrated under reduced pressure to give a yellow solid. To this solid was added water (100 mL), which was then removed under reduced pressure. Toluene (100 mL) was similarly added and removed under reduced pressure, and then dichloromethane (200 mL) was added to the residue and the resultant solution was filtered and concentrated to produce a yellow oil. Hexanes (200 mL) were added and the resultant solution was cooled to induce crystallization. After recrystallization from hexanes, the desired compound was isolated as tan crystals (4.28 g, 33% yield over Parts A and B). The structure of this compound was confirmed by mass spectroscopy and by $^1$H and $^{13}$C NMR spectroscopy.

Part C: Preparation of 4-hexyl-3-(p-vinylbenzyloxy)-cyclobut-3-en-1,2-one

Triethylamine (1.75 g, 17.3 mmol), 2,6-di-t-butyl-4-methylphenol (a radical inhibitor, 0.7 mg, 3.4 μmol) and 4-vinylbenzyl chloride (5.04 g, 33 mmol) were added, in that order, to a solution of 3-hexyl-4-hydroxy-cyclobut-3-en-1,2-one (3.0 g, 16.5 mmol, prepared in Part B above) in chloroform (90 mL), and the resultant solution was heated at reflux for 7 hours. The solution was then cooled and allowed to stand overnight at room temperature, after which it was heated at reflux for a further 7 hours, then cooled and allowed to stand overnight a second time. The reaction mixture was then concentrated under reduced pressure, the residue dissolved in dichloromethane (150 mL), and the resultant solution washed with water (2×75 mL), dried over magnesium sulfate and concentrated under reduced pressure to yield a yellow oil, which was purified by short-path distillation (to remove excess 4-vinylbenzyl chloride) at 72°–74° C. and 1.7 mm Hg pressure. The residue from the distillation was purified by flash chromatography on silica gel with dichloromethane as eluant to give the desired compound (1.23 g, 25% yield) as a golden oil. The structure of this compound was confirmed by mass spectroscopy and by $^1$H and $^{13}$C NMR spectroscopy.

EXAMPLE 8

Preparation of 3-methylamino-4-(p-vinyl-benzyloxy)cyclobut-3-ene-1,2-dione

This Example illustrates the preparation of 3-methylamino-4-(p-vinylbenzyloxy)-cyclobut-3-ene-1,2-dione, the compound of Formula I in which $R^2$ is a amino group and $R^1$ is an p-vinylbenzyl group.

Part A: Preparation of bis(4-vinylbenzyl) squarate

4-Vinylbenzyl chloride (13 g, 85 mmol) was added to a suspension of silver squarate (freshly prepared from squaric acid (5.5 g, 48 mmol) by the method described in S. Cohen et al., J. Am. Chem. Soc., 88, 5433 (1966)) in dry ether (100 mL), and the resultant mixture was stirred in the dark for 3 days. The reaction mixture was then filtered and the solvent removed under reduced pressure. The residue was taken up in dichloromethane and filtered through a short column of silica gel, then concentrated under reduced pressure, to yield the desired compound in a crude form, which was used in Part B below without further purification.

Part B: Preparation of 3-methylamino-4-(p-vinylbenzyloxy)-cyclobut-3-en-1,2-dione The crude product from Part A above was dissolved in ether (300 mL) and gaseous methylamine was bubbled through this ether solution for 1 minute. The resultant mixture was allowed to stand for 5 minutes, then the precipitate which had formed was removed by filtration, redissolved in chloroform and filtered through Celite (manufactured by Johns-Manville Corporation, Denver, Colo. 80217). The solvent was removed under reduced pressure to give Compound H as a colorless oil (3.5 g, 30% yield over Parts A and B). The structure of this compound was confirmed by $^1$H NMR spectroscopy.

EXAMPLE 9

Preparation of copolymer of Compound H with lauryl methacrylate

This Example illustrates the preparation of a 1:1 w/w copolymer of Compound H prepared in Example 8 above with lauryl methacrylate.

Compound H (1 g) and lauryl methacrylate (1 g) were dissolved in a mixture of 2-propanol (30 mL) and ethanol (20 mL), and the resultant solution was purged with nitrogen. Azaisobutyronitrile (0.01 g) was then added, and the solution was held at 65° C. overnight, during which time a precipitate (250 mg) formed. This precipitate was collected and shown by infra-red spectroscopy to contain squarate esters.

EXAMPLE 10

Preparation of 4-[5-[1,2-dioxo-3-hydroxycyclobut-3-en-4-yl]pent-1-yl]3-hydroxycyclobut-3-ene-1,2-dione Pentamethylenebis(magnesium bromide) (25 mL of a 0.5M solution in THF, 12.5 mmol) was added dropwise over a period of 15 minutes to a solution of dibutyl squarate (5.66 g, 25 mmol) in dry THF (50 mL) at −78° C. under a stream of nitrogen. The resulting suspension was stirred at −78° C. for 1 hour, then allowed to warm to room temperature and stirred for a further 2 hours. The homogeneous yellow solution which resulted was cooled to 0° C., and water (10 mL) was added dropwise over a period of 2 minutes. After standing for 5 minutes, the solution was diluted with THF (50 mL) and washed with saturated sodium chloride solution (150 mL). An emulsion was formed, which was separated by evaporative removal of THF and addition of dichloromethane (200 mL). The organic layer was separated and the aqueous layer was extracted with more dichloromethane (100 mL). The combined dichloromethane layers were dried over magnesium sulfate and concentrated under reduced pressure to yield a golden oil which was shown by thin layer chromatography, on silica gel with 1:1 ether/hexanes as eluent, to consist of five components.

This mixture was separated by flash chromatography on silica gel with 1:1 ether/hexanes, followed by pure ether, as eluents. Each of the five components was examined by $^1$H NMR spectroscopy. The third and fourth components (in order of elution from the column) were tentatively assigned as 4-[5-[1,2-dioxo-3-butoxycyclobut-3-en-4-yl]pent-1-yl]-3-butoxycyclobut-3-ene-1,2-dione (0.69 g) and 2,3-dibutoxy-[5-[1,2-dioxo-3-butoxycyclobut-3-en-4-yl]pent-1-yl]-4-hydroxycyclobut-2-ene-1-one (2.14 g).

A portion of the isolated fourth component (2.01 g) was dissolved in THF (20 mL), and the resultant solution was treated with 6M hydrochloric acid (20 mL). The two-phase mixture became warm, and after 15 minutes stirring was observed to have become homogeneous. After a further two hours stirring, the solution was concentrated to dryness under reduced pressure. Water (20 mL) was added, and removed evaporatively, in order to drive off excess hydrogen chloride. The remaining water was removed by azeotropic distillation under reduced pressure with dichloromethane/acetone, to yield an off-white solid. This material was purified by recrystallization from THF/ether to yield the desired compound as a tan powder (542 mg, 18% yield over two steps). The structure of this compound was confirmed by $^1$H and $^{13}$C NMR spectroscopy.

EXAMPLE 11

Preparation of 4-[5-[1,2-dioxo-3-[4-methyl-benzyloxy]cyclobut-3-en-4-yl]pent-1-yl]-3-[4-methylbenzyloxy]cyclobut-3-ene-1,2-dione This Example illustrates the preparation of a dimeric squaric acid derivative in which two 4-methylbenzyloxy]cyclobut-3-ene-1,2-dione groups are linked via a pentamethylene chain.

Triethylamine (423 mg, 4.18 mmol) and p-methylbenzyl bromide (1.47 g, 7.96 mmol) were added sequentially to a suspension of 4-[5-[1,2-dioxo-3-hydroxycyclobut-3-en-4-yl]pent-1-yl]-3-hydroxy-cyclobut-3-ene-1,2-dione (526 mg, 2.0 mmol, prepared in Example 10 above) in chloroform (15 mL) at room temperature, and the mixture was then heated at reflux for 9 hours. The solvent was removed under reduced pressure, and the resultant oil was purified by flash chromatography on silica gel with dichloromethane, followed by ether, as eluents. The product eluted with ether, and was obtained as a yellow oil (591 mg, 63% yield). The structure of this compound was confirmed by $^1$H and $^{13}$C NMR spectroscopy.

EXAMPLE 12

Polymerization process of the invention

This Example illustrates a process of the present invention in which the superacid generated after infra-red and ultra-violet irradiation is used to cause polymerization of a difunctional epoxy monomer.

A coating fluid was prepared by dissolving a silicone diepoxy monomer of the formula:

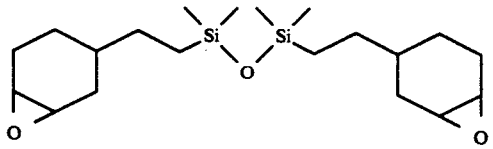

(supplied by General Electric Company, 40 mg), t-butyl-anthracene (5 mg; a precursor sensitizer), an infrared dye of the formula:

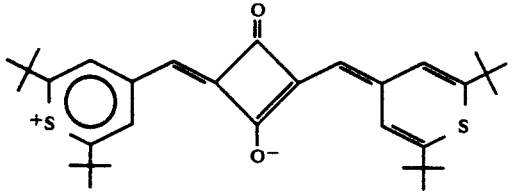

(see U.S. Pat. No. 4,508,811, 0.3 mg), (4-octyloxyphenyl)phenyliodonium hexafluoroantimonate (8 mg, prepared as per U.S. Pat. No. 4,992,571), and poly(vinyl chloride) (supplied by Aldrich Chemical Company, Milwaukee, Wis., 30 mg) in methyl ethyl ketone (MEK, 0.6 mL). This solution was coated on to a poly(ethylene terephthalate) base 4 mil (101 μm) in thickness (ICI Type 3295, supplied by ICI Americas, Inc., Wilmington, Del.) using a number 18 coating rod.

The coated side of the resultant coating was exposed to infra-red radiation from a GaAlAs semiconductor diode laser emitting at 822 nm, which delivered 125 mW to the medium. The laser output was focussed to a spot approximately 33×3 μm. The medium was wrapped around a drum whose axis was perpendicular to the incident laser beam. Rotation of the drum about its axis and simultaneous translation in the direction of the axis caused the laser spot to write a helical pattern on the medium. The pitch of the helix was 33 μm, chosen so that none of the medium was left unexposed between adjacent turns. In this arrangement, the exposure received by the medium was inversely proportional to the speed of rotation of the drum (here measured as a linear speed at the medium surface). Separate bands of the medium were exposed at 2.0, 2.5, 3.0, 3.5 and 4.0 m/s. Following this infra-red exposure, the entire coating was exposed for 70 seconds to ultra-violet radiation from a Universal UV unit (nominally emitting at 375 nm) supplied by Gelman Instrument Company. The coating was next heated on a hotplate at 100° C. for 20 seconds, after which the coating was developed by washing sequentially with methyl ethyl ketone and dichloromethane. Residual material was finally removed by sonication in a bath of methyl ethyl ketone for three minutes. In all areas which had received the infra-red exposure, insoluble polymeric material remained adhering to the polyester base and was not removed by the solvent treatment or sonication, whereas in all other areas of the film, including those areas which had received ultra-violet but not infra-red irradiation, no polymeric material was left adhering to the base after these treatments.

EXAMPLE 13

Imaging process of the invention using an acid generator

This Example illustrates an imaging process of the invention in which the imaging medium contains a secondary acid generator which amplifies the free superacid present in infra-red exposed areas following the infra-red and ultra-violet irradiations.

Two coating fluids were prepared as follows:

Fluid A: t-Butyl-anthracene (7 mg), the infra-red dye described in Example 12 above (0.3 mg), (4-octyloxyphenyl)phenyliodonium hexafluoroantimonate (5 mg), 3,4-bis(4-methylbenzyloxy)cyclobut-3-en-1,2-dione (20 mg) and a copolymer of vinylidiene chloride and acrylonitrile (Saran Resin F120, available from Aldrich Chemical Company, Milwaukee, Wis., 30 mg) were dissolved in methyl ethyl ketone (0.6 mL).

Fluid B: A leuco dye of the formula:

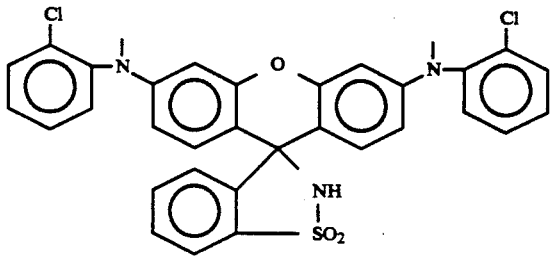

(15 mg; this leuco dye may prepared by the procedure described in U.S. Pat. No. 4,345,017) and a hindered amine base (HALS-62, available from Fairmount Chemical Company, Inc., 117 Blanchard Street, Newark N.J. 07105, 7 mg) were dissolved in 1:1 MEK:-chloroform. Saran Resin F120 (available from Aldrich Chemical Company, Milwaukee, Wis., 30 mg) dissolved in methyl ethyl ketone (0.3 mL) was added to the resultant solution.

These coating fluids were separately coated on to poly(ethylene terephthalate) base of 4 mil (101 μm) in thickness (ICI Type 3295, supplied by ICI Americas, Inc., Wilmington Del.) using a number 18 coating rod to form Films A and B respectively.

Film A was exposed through the polyester base to infra-red radiation from a GaAlAs semiconductor diode laser in the same way as in Example 12 above. Following the infra-red exposure, the entire coated side of Film A was exposed to the unfiltered output of a low pressure mercury UV lamp, model B-100 (supplied by Black Light Eastern, a division of Spectronics Corporation, Westbury, Long Island, N.Y.) for 47 seconds. Film A was next heated on a hotplate at 117° C. for 15 seconds, after which it was laminated at 240° F. (116° C.) and 60 psi (0.4 MPa) to Film B, with the two coated sides in contact. Table 2 below shows the green optical densities achieved for various infra-red exposures; these densities were measured using an X-Rite 310 photographic densitometer, supplied by X-Rite, Inc., Grandville, Mich., with the appropriate filter.

TABLE 2

| Scanning speed (m/sec) | Green optical density |
| --- | --- |
| No IR exposure | 0.07 |
| 2.0 | 2.68 |
| 2.5 | 2.81 |
| 3.0 | 2.73 |
| 3.5 | 2.69 |
| 4.0 | 2.95 |

From the data in Table 1, it will be seen that the green optical density achieved in the imaged areas was independent of the scanning speed within the range shown in Table 1. Further experiments indicated that at higher scanning speeds, very little magenta dye density developed, presumably because so little superacid was generated during the infra-red irradiation that, even after the ultra-violet irradiation, the quantity of superacid generated did not exceed the threshold required to protonate all the infra-red dye and hence leave free superacid present in the infra-red exposed areas. Accordingly, at these high scanning speeds, even in the infra-red exposed areas, there was no free superacid available to catalyze the decomposition of the acid generator, so little or no production of the second acid took place and little magenta color developed.

Further experiments also indicated that if the ultraviolet exposure was less than 40 or more than 55 seconds, no significant difference in optical density was seen between the areas which had received infra-red irradiation and those which had not; if the ultra-violet irradiation was too short, little or no dye density developed in any part of the film, while if the ultra-violet irradiation was too long, the whole film developed the maximum dye density. Presumably, if the ultra-violet irradiation is too short and thus too little superacid precursor is decomposed during this irradiation, even in infra-red exposed areas the quantity of superacid present following the ultra-violet irradiation will not exceed the aforementioned threshold, no free superacid will be present in the infra-red exposed areas during the heating step, no acid amplification will occur, and little or no magenta dye density will result. On the other hand, if the ultra-violet irradiation is too long and thus too much superacid precursor is decomposed during this irradiation, even in areas not exposed to infra-red radiation the quantity of superacid present following the ultra-violet irradiation will exceed the aforementioned threshold, free superacid will be present throughout the film and acid amplification and dye color change will occur in all areas.

EXAMPLE 14

Imaging process of the invention using a single sheet medium

This Example illustrates an imaging process of the invention generally similar to that in Example 13 above, but in which the imaging medium comprises a single sheet rather than two sheets which are laminated together following the ultra-violet irradiation.

Two dispersions were prepared as follows:

Dispersion A

De-ionized water (60 mL) was added dropwise to a magnetically stirred solution of a surfactant (Aerosol TR-70, adjusted with potassium hydroxide to pH 6, 0.65 g), the leuco dye used in Example 13 above (2.5 g), a base (HALS-62, supplied by Fairmount Chemical Company, 0.25 g) and a polymeric binder (Elvacite 2043, supplied by DuPont de Nemours, Wilmington, Del., 2.75 g) in dichloromethane (46 mL). The resultant, very viscous mixture was sonicated, causing the viscosity to decrease, and then the mixture was allowed to stir overnight at room temperature, during which time the dichloromethane evaporated. A fluorinated surfactant (FC-120, supplied by Minnesota Mining and Manufacturing Corporation, St. Paul, Minn., 56 mg of a 25% aqueous solution) was then added.

Dispersion B

De-ionized water (53.5 mL) was added dropwise to a magnetically stirred solution of a surfactant (Aerosol TR-70, adjusted with potassium hydroxide to pH 6, 0.58 g), a base (HALS-63, supplied by Fairmount Chemical Company, 2.45 g) and a polymeric binder (Elvacite 2043, supplied by DuPont de Nemours, 2.45 g) in dichloromethane (53.5 g). The resultant, very viscous mixture was sonicated, causing the viscosity to decrease, and then the mixture was allowed to stir overnight at room temperature, during which time the dichloromethane evaporated.

2 mL of Dispersion A was then combined with 1 mL of Dispersion B and poly(vinyl alcohol) (Vinol 540, supplied by Air Products Corporation, Allentown, Penn., 1 mL of 5% aqueous solution). The resultant coating fluid was then overcoated, using a number 8 coating rod, on to Film A prepared in Example 10 above.

The imaging medium thus prepared, which comprised a single sheet having both an acid-generating layer and a color-forming layer, was exposed through the polyester base to infra-red radiation from a GaAlAs laser in the same manner as in Example 12 above. Following this infra-red irradiation, the entire coating was exposed for 200 seconds, through the polyester base, to ultraviolet radiation from the aforementioned low pressure mercury UV lamp, model B-100 equipped with a 365 nm interference filter (supplied by Corion Corporation, Holliston, Mass.). The power measured at the film plane in the arrangement used was 0.3 mW/cm². The coating was then heated on a hotplate at 115° C. for 60 seconds. Table 2 below shows the green optical density achieved for various infra-red exposures, measured in the same manner as in Example 11 above.

TABLE 3

| Scanning speed (m/sec) | Green optical density |
|---|---|
| No IR exposure | 0.03 |
| 2.0 | 1.04 |
| 2.5 | 1.34 |
| 3.0 | 1.35 |
| 3.5 | 0.97 |
| 4.0 | 0.41 |

From the data in Table 2, it will be seen that the optical density achieved was independent of scanning speed only for scanning speeds below 3.5 m/s. Presumably, at higher scanning speeds, too little superacid precursor is decomposed during the infra-red irradiation, so that even in infra-red exposed areas the quantity of superacid present following the ultra-violet irradiation will not exceed the aforementioned threshold, little or no free superacid will be present in the infra-red exposed areas during the heating step, little or no acid amplification will occur, and a reduced magenta dye density will result.

From the foregoing, it will be seen that the present invention provides a process for generation of a superacid (and optionally a strong second acid) using radiation of wavelengths (preferably near infra-red wavelengths) to which conventional superacid precursors are not sensitive. The superacid or second acid thus generated can be used to carry out any acid-dependent reaction for which superacids and other acids have hitherto been used. In particular, preferred embodiments of the invention permit the production of high resolution images using infra-red lasers, with high sensitivity of the imaging medium.

I claim:

1. A process for generation of free superacid, which process comprises:
   providing a medium containing a mixture of a superacid precursor and a dye capable of absorbing actinic radiation of a first wavelength which does not, in the absence of the dye, cause decomposition of the superacid precursor to form the corresponding superacid, the superacid precursor being capable of being decomposed by actinic radiation of a second wavelength shorter than the first wavelength;
   irradiating part of the medium with actinic radiation of the first wavelength, thereby causing, in the irradiated part of the medium, absorption of the actinic radiation, and decomposition of part of the superacid precursor, without formation of free superacid but with formation of a protonated product derived from the dye; and
   thereafter irradiating a larger portion of the medium with actinic radiation of the second wavelength, thereby causing, in the part of the medium exposed to the radiation of both the first and second wavelengths, decomposition of part of the remaining superacid precursor, with formation of free superacid without generation of free superacid in the part of the medium exposed to the radiation of the second wavelength but not to the radiation of the first wavelength.

2. A process according to claim 1 wherein the medium is imagewise exposed to the actinic radiation of the first wavelength so that the free superacid generated in the areas of the medium exposed to the actinic radiation of the first wavelength forms an image.

3. A process according to claim 2 wherein the medium further comprises a monomer or oligomer which polymerizes in the presence of the free superacid, so that, in the part of the medium exposed to the radiation of both the first and second wavelengths, the monomer polymerizes, but in the part of the medium not exposed to the radiation of the first wavelength, the monomer remains substantially unpolymerized.

4. A process according to claim 2 wherein the medium further comprises a polymer which depolymerizes in the presence of the free superacid, so that, in the part of the medium exposed to the radiation of both the first and second wavelengths, the polymer depolymerizes, but in the part of the medium not exposed to the radiation of the first wavelength, the polymer remains substantially polymerized.

5. A process according to claim 2 wherein the medium further comprises a polymer the solubility of which in a solvent changes in the presence of the free superacid, and, following exposure of the medium to the radiation of both the first and second wavelengths, the polymer is treated with said solvent, whereby the polymer is removed from one of the exposed and unexposed areas of the medium, but the polymer is not removed from the other of said areas.

6. A process according to claim 2 wherein the medium further comprises a polymer the adhesion of which to a material changes in the presence of the free superacid, and, following exposure of the medium to the radiation of both the first and second wavelengths, the polymer is contacted with said material, whereby one of the exposed and unexposed areas of the medium adheres to said material, while the other of said areas does not adhere to said material.

7. A process according to claim 1 for generation of free superacid and subsequent generation of a second acid, wherein, following the irradiation with the actinic radiation of the second wavelength, the medium containing the free superacid is heated while the superacid is admixed with a secondary acid generator capable of superacid-catalyzed decomposition to form a second acid, such that, in the part of the medium irradiated with the actinic radiation of the first wavelength, the superacid catalyzes the thermal decomposition of the secondary acid generator and the second acid is formed, whereas the part of the medium not irradiated with the actinic radiation of the first wavelength remains essentially free from the second acid.

8. A process according to claim 1 wherein the first wavelength is in the range of about 700 to about 1200 nm and the dye is an infra-red dye capable of absorbing infra-red radiation within this wavelength range.

9. A process according to claim 8 wherein the dye is a squarylium dye.

10. A process according to claim 1 wherein the superacid precursor comprises an iodonium compound.

11. A process according to claim 10 wherein the superacid precursor comprises a diphenyliodonium compound.

12. A process according to claim 1 wherein the second wavelength is in the range of about 400 to about 180 nm.

13. A process according to claim 7 wherein the secondary acid generator is a squaric acid derivative and the second acid generated therefrom is squaric acid or an acidic derivative thereof.

14. A process according to claim 13 wherein the squaric acid derivative is a 3,4-disubstituted-cyclobut-3-ene-1,2-dione in which at least one of the 3- and 4-substituents consists of an oxygen atom bonded to the squaric acid ring, and an alkyl or alkylene group, a partially hydrogenated aryl or arylene group, or an aralkyl group bonded to said oxygen atom, said 3,4-disubstituted-cyclobut-3-ene-1,2-dione being capable of decomposing so as to cause replacement of the or each original alkoxy, alkyleneoxy, aryloxy, aryleneoxy or aralkyloxy group of the derivative with a hydroxyl group, thereby producing squaric acid or an acidic squaric acid derivative having one hydroxyl group.

15. A process according to claim 15 wherein the squaric acid derivative is of one of the following formulae:

a. 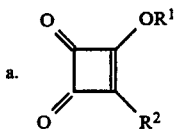

in which $R^1$ is an alkyl group, a partially hydrogenated aromatic group, or an aralkyl group, and $R^2$ is a hydrogen atom or an alkyl, cycloalkyl, aralkyl, aryl, amino, alkylamino, dialkylamino, alkylthio, alkylseleno, dialkylphosphino, dialkylphosphoxy or trialkylsilyl group, subject to the proviso that either or both of the groups $R^1$ and $R^2$ may be attached to a polymer;

b. 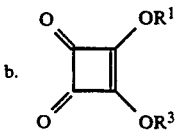

in which $R^1$ and $R^3$ independently are each an alkyl group, a partially hydrogenated aryl group or an aralkyl group, subject to the proviso that either or both of the groups $R^1$ and $R^3$ may be attached to a polymer; and c. 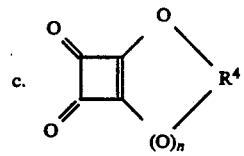

in which n is 0 or 1, and $R^4$ is an alkylene group or a partially hydrogenated arylene group;

or the squaric acid derivative comprises at least one unit of the formula:

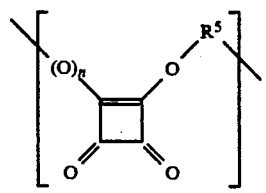

in which n is 0 or 1, and $R^5$ is an alkylene or partially hydrogenated arylene group.

16. A process according to claim 7 wherein the second acid is contacted with an acid-sensitive material which changes color in the presence of the second acid.

17. A process according to claim 16 wherein, prior to the heating, the acid-sensitive material is in admixture with an amount of a basic material insufficient to neutralize all the second acid liberated by the secondary acid generator during the heating, so that the second acid liberated during the heating neutralizes all of the basic material and leaves excess second acid sufficient to effect the change in the acid-sensitive material.

18. A process according to claim 17 wherein, prior to the heating, the acid-sensitive material is present in a layer or phase separate from the layer or phase containing the superacid precursor and the secondary acid generator, and following the generation of the second acid, the two layers or phases are mixed, thereby effecting the change in the acid-sensitive material.

* * * * *